United States Patent [19]

Basbaum et al.

[11] Patent Number: 6,136,539
[45] Date of Patent: Oct. 24, 2000

[54] COMPOSITIONS AND METHODS FOR THE INHIBITION OF MUC-5 MUCIN GENE EXPRESSION

[75] Inventors: Carol Basbaum, San Francisco; Marianne Gallup, Greenbrae; Daizong Li, San Francisco; Assefa Gebremichael, Berkeley; Erin Gensch, San Francisco, all of Calif.

[73] Assignee: The Regents of the University of California, Oakland, Calif.

[21] Appl. No.: 09/248,571

[22] Filed: Feb. 11, 1999

Related U.S. Application Data

[60] Provisional application No. 60/074,398, Feb. 11, 1998.

[51] Int. Cl.$^7$ .............................. C12Q 1/68; C12N 5/00; C12N 15/00; C07H 21/02; C07H 21/04
[52] U.S. Cl. ........................... 435/6; 435/320.1; 435/325; 536/23.1; 536/24.1; 536/24.2; 536/24.3
[58] Field of Search ........................... 435/6, 320.1, 325; 514/1; 536/23.2, 23.1, 24.2, 24.1; 530/350

[56] References Cited

FOREIGN PATENT DOCUMENTS

WO 97/43643  11/1997  WIPO .......................... G01N 33/536

OTHER PUBLICATIONS

Gendler et al., Abstract #290. Pediatric Pulmonology Supp. 13 (1996).
Hovenberg et al., Biochemical Journal 318:319–324 (1996).
Gendler S et al., Annu. Rev. Physiol. 57:607–634 (1995).
Li et al., Transcriptional activation of mucin by *Pseudomonas aeruginosa* lipoplysaccharide in the pathogenesis of cystic fibrosis lung disease. Proc. Natl. Acad. Sci. USA, vol. 94, pp. 967–972, Mar. 1997.
Meerzaman et al., Cloning and Analysis of cDNA encoding a major airway glycoprotein, human tracheobronchial mucin (MUC5). Journal of Biological Chemistry, vol. 269, No. 17, pp. 12932–12939, Mar. 1994.
Duperat et al., Characterization of the human mucin gene MUC5AC: a consensus cysteine–rich domain for 11p15 mucine genes? Biochemical Journal, vol. 305, pp. 211–219, Mar. 1997.
Boucher et al., "Mucoid *Pseudomonas aeruginosa* in Cystic Fibrosis: Characterization of muc Mutations in Clinical Isolates and Analysis of Clearance in a Mouse Model of Respiratory Infection," Infection and Immunity, vol. 65, No. 9, pp. 3838–3846, 1997 (A).
Li et al., "Cloning of the Amino–terminal and 5'–Flanking region of the Human MUC5AC Mucin Gene and Transcription Up–regulation by Bacterial Exoproducts," J. Bio. Chem., vol. 273, No. 12, pp. 6812–6820, 1998 (Y).

*Primary Examiner*—Stephanie W. Zitomer
*Assistant Examiner*—C. Wilder
*Attorney, Agent, or Firm*—Cooley Godward LLP

[57] ABSTRACT

The invention relates to methods for identifying inhibitors of mucin production, methods for inhibiting mucin production and methods for treating airway diseases, such as cystic fibrosis, chronic bronchitis, bronchial pneumonia and asthma. Compositions are provided for use in the method comprising reporter gene constructs which are inducible by mucomones.

19 Claims, 6 Drawing Sheets

First Nucleotide is    -3752

GGTCGACGGCCCGGGCTGGTCTGGACCCCAGCAGCGGCCCTGGGTGACGTCTGGCTGAGGGAGG
AGAAAGCTGTGGCTGGGGCGGCAAGGCCTGGGTGGCCAGTTGGCCAGGTGCCCCGGGGCTTGGC
CCAGCCTCAGACACGCAGGGGGCACTCCCCTCTGAGGGCCACGCTGGTGACTCAGACTGTTCAG
AGGTCACGGTATGGACTGGGCCAGTGACTCAGGCCTGTCCTCTGTTGGGGGCTGGACACTGACT
CACCCACTGCCTCCTGTCTATCTGAGGGCGTAAGGAGGGCAGGCCTTCAGGCACTCACATGCGG
CCCTGGCCAGGGTCCCGGTCACACCTGCAGACCCTCAAGCCCTTCCCTATGCCCCACTGACATA
ACCACCTGGCCCTGGGATCTGGTCCCACCGCGGGGCCCATTGTCCACTACCAGGACCCTCCTCT
GCCTTCATCAGCACCAGGCGACCTGGTGTCCACTCCTGGGCCAGGGCAGGGGAACCCTGGCTAC
ACCTGGTCGAGTCAGACCTCCCGAAGCACCAGTGGCTGGGGTGGTCCACCCTAACCCTGTCAGC
CGCTCAGCCTTAAATGTGATCACTCGCTCAGTCAGTCGCCACCCACTCACTCACTCACCCACTC
ACTTATTCACTCACTCACCCACTCACTTATTCACCCATTCACTCATTCACTCACCCATTCACTC
ACTCACTTATTCACTCACTCTCTCACTCATTCATTAATTCGCCCATTCACTCACACTTTCACTC
ACTCACTTATTCACTCATACACTCATTCACTTATTTACTCACTCATTCACTCACTCATTAATTC
ACCCATTCACTCACTCACTTATTCACTCATAGACTCATACACTCACTCATTCACTCACGCATCC
ACTCATTCACTCACTCATTTACCCACTCATTCACTCATTCACTCACTCACTCATTTATTCACCC
ATTCACTCATTCATTCACTCACTCACTGACTCATTGACTCATTCCCTCACTCATTCACCCATTC
ACTTACTCATTCACTCACCCATTTATTCACTCACTCACTCATTTACTCATTCATTCACCCATTC
ACTCACTCACTGACTCATTGACTCATTCACTCATTCACCCATTCACTTACTCACTCACTCATTT
ACTCACTCATTCATTCATTGACTCATTAACTCATTCCCTCTCATTCACTCACTCACTGACTC
ATTAACTCATTCACTCTCTCATGCATCCACTCATTCACTCACTCACTGACTCACTCATTCACTC
ACTCATTGACTCACTCATTTGGTTATTCACTCATTCACTCACTCACTGACTCATTCACTCACTC
ATTCACTGCTCACTTATTCACTCTTTCACTATCTCTTTCATTCACATTCATTCATTAACTCAGT
CACTCACTCATTCACTCTCACTCATTCACTTACTCATTTACTCATTCACTCATCTATTCATTCA
CTCATTCACTCACTCATTCATTCACCCATTCACTCATTCATTCACCCATTCACTCACTCACTTA
TTCACTCATAGACTCATACACTCACTCACTCATTGACTCACTCACTCATTCACTCATGCATCCA
CTCATTCACTCACTCATTTACTCACTCACTCATCCACTCACTCACTCATTCATTCACCCA
TTCACTCAATCATTCATTCACTCACTCACTGACTCATTGACTCATTCCCTCACTCATTCACCCA
TTCACTTATTCATTCACTCACCCATTTATTCACTCACTCACTCATTTACTCACTCACTCACTCA
TTTACTCATTCCATTCACCCATTCACTCACTCATTCACTCACTCACTAACTCATTGACTCATTC
ACTCACTCATTCCCCCTTCACTTACTCACTAACTTATTACTCACTCATTCACTCACTCATTCA
TTGACTCATTAACTCATTCACTCTTTCACTCACTCACTGACTCATTCACTCATTCACTCACTCA
TTCACTCACTCACCCACTCATTGACTCACTCATTCACTTATTCACTCATTCACTCACTCACTGA
CTCATTCACTCATTCACTGCTTGCTTATTCACTCTTTCACTATCTCTCATTCACATTTATTC
ATTAACTCAGTCACTCACTCATTCACTCTCATTCACTTACTCATTTACTCACTCATTTACTC
ATTCACTCTCTCATTCACTTACTCATTTACTCACTCATTTACTCACTCACTCACCTGTTCACTC
ACTCGCTCACTCATTCACATTCATTTAACTCACTCATTTACTCATAGACTCACTCATTTATCC
ACTCACTTATTCATTACCTCATTCATTCACTCACTCAATCATTTTCCCTTTCCCCACACTCCTG
CCACATGTGAAGTGCTCTTTCTCTAGGCACCTGGGCTAAGACAGGACATGGGGAGGGAAAGGCA
CAGAAATGGAGAAGTAGGCAATCATAAAGAGCTTGGGACGGGTCCCTAGAGAGCTGGAAGCAAG
TGCTCAGAACAGCCTTGAGGCACCTCTTCGACCCTAACCCCTCTGCAGCAGGACAAAGGGCCCA
GCCCAGCCTCTCCCTTTCCTGCCATTCCTCCCATGGGAGACCTTCTGGTTGGACGCTCCACATG
GGCAGTGGAGCAGCCGACCTTGGCTGGGGAGTGTGTGGCTGCCTGGGAGGGAGAGTCTAGCCAC

FIG._1A

AGTGTCCAGCCACACACCTGTGGTCTGGGCAAGTGTTCATCACACAACAGCACCTTCTCAGCCA
GAGCCCTTCAGGCCAAAGACTCACTGGGACCTTTCTGTGCTGGGACTGCTCGGACCAGTCAACA
GCTTCCTGTCCAGAGGGTACTGAGCATTTCTGGATCTTGGTGGCCAGAGACCATCAAGTGACTT
GAACTGGCCCTGCCCGCCTGGGGTCAGGAGACAGAAGCACAGGTGGACTCCTGGGCAATGCTGG
GAGGGGGCTGCATGGTGAGGGAGGGGTTCTATCATTTGCCTGGAGGCTGCTGCCAGGAGCCCCT
CTCCAGGGAGGGTGAGGCTGGCTGGCGCTACTTCAGTGGCAGCATGTGGCTGGCCTGAGGGACG
CCTTGGCTCACTCACTCCTCAATCACTCATTTACTCATTCATTCACTCACTCAATCATTTTTCC
TTTCGCCACACTCCTGCCGCATGTGCTCTCTCTAGGCATCCGGGTAAGACAAGACATGGGGA
GTAAAAGGCACAGAAATGGAGAAATAGGTGACCATAAGGAGCTTTGGATGGGGCTGGGGCTGGC
CTCTCCCTCCCAGGCAGCCACACATTCCCCAGCCAAGGTCGGCAGCTCCACTGCCCATGTGGAG
GGTCCAACCAGGAGGTCGGCCATGGGAGGAATGGCAGGAAAGGGAAAGGCTGGGCTGGGCCCCC
TGTCCTGCTGCAGAGGGATTAGTGTCAAAGAGGTGCCTTAAGGCTGTTCTGAGCACTCACTTCT
GGGCACCAGGAACTCACAGGCTGCTGGGCATGGCACGGTGCCCAGGGAGAGTCTAGGGTGGGGT
ATGTGGGGAGGACCCCTGCAGGCCAGGGCTTGGGGGGGCCCTCGGAAACTGGGCTCTACCCGGC
AGACACACCCATCTCCGCCTGCCACCGGCCGCTGGCCAGCCCGCAGTGAGCACCCACTGTTTAC
TTGGGTGAGGGGAACCACAGGCCCCGCCCTGCCCACCCACGTGAAGCACGGGGCTGGAGCCAG
CTCTGGGGCTACAAAAGCTCCTGCCACCTTGGGTCCCTCCTCAGAGGCTGCTGAGGGACAGGG
CACTCTTCCCCGCCGTCCACACAATGAGTGTTGGCCGGAGGAAGCTGGCCCTGCTCTGG

FIG._1B

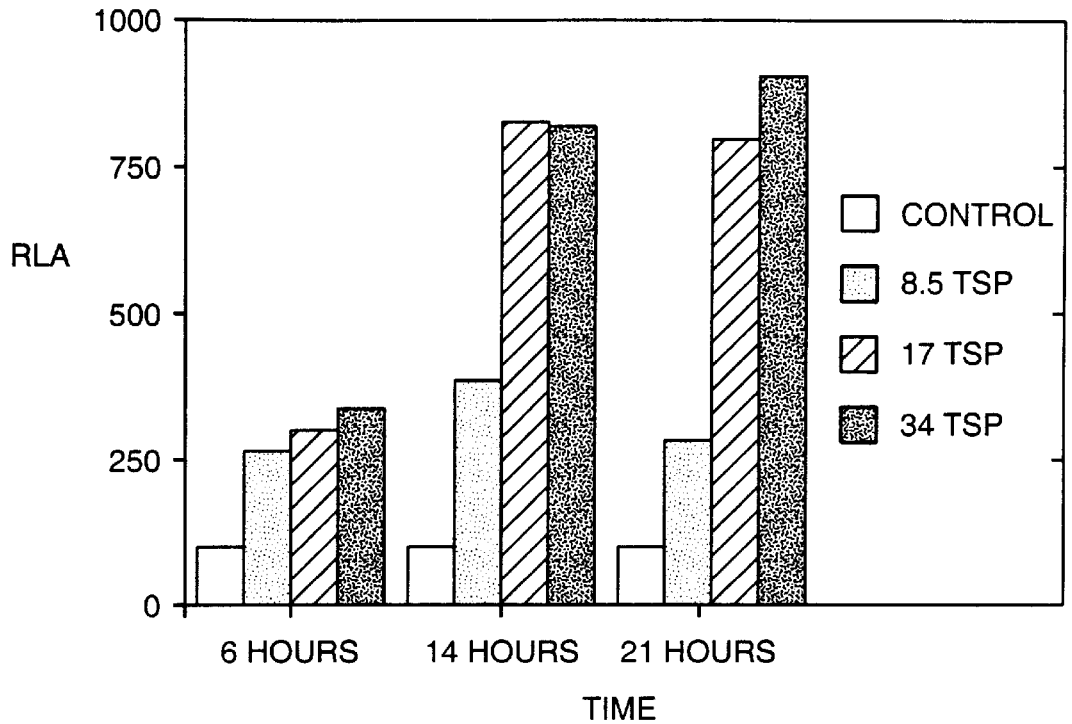
FIG._2
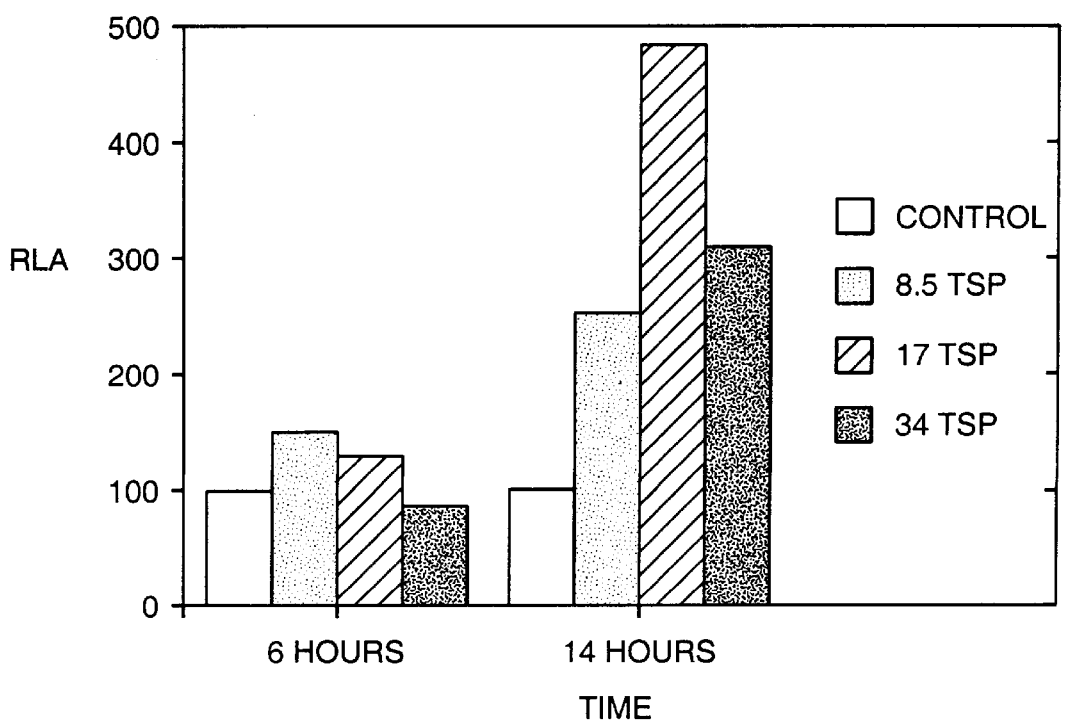
FIG._3

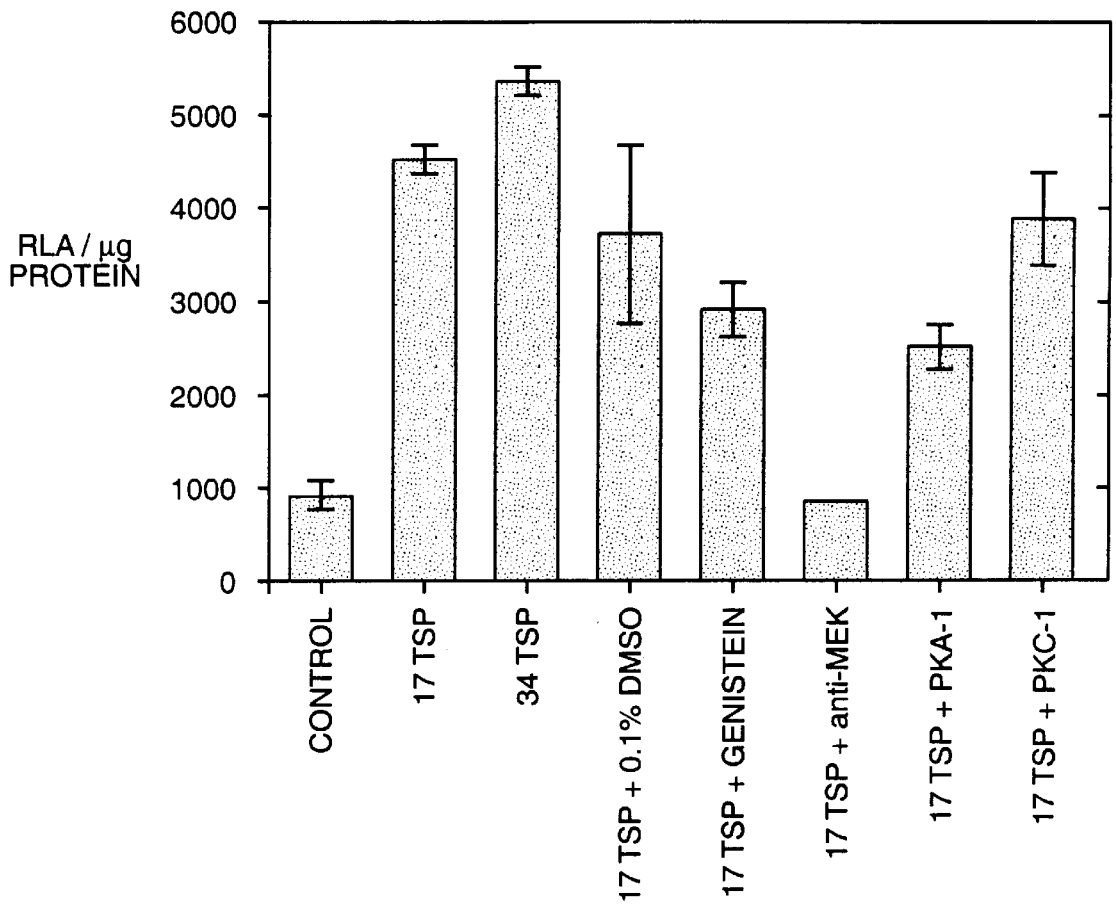

FIG._4

CCACCTTGGGTCCCTCCTCAGAGGCTGCTGAGGGACAGGGCACTCTTCCCCGCCG
TCCACACAATGAGTGTTGGCCGGAGGAAGCTGGCCCTGCTCTGGGCCCTGGCTCT
CGCTCTGGCCTGCACCCGGCATACAGGTACGGCTTGGCCCTGGGCCCTCTACTGG
TCCTGGGTGGTGCGGTACTGAGTGGGCCTCAGCAGCTCAGTCTTTGCCCTGGGCA
GGCTGCATTGTGCCATGAACGGCTCCCAGCAGCATAGCCCCTGACTGTGGCCTGG
CAGAACGAGCAGTTTCCCTTGTGGTTGGGAAGGGATCTCTGGGCTTCGCGACCTC
TGAGCTGGCATTCCTGAGCAGGAAGTAGAGCTCAGATCTCGGCTTTCCTCTGCCG
ATCCTGCACTGTCCCAGAAGCGAAGACTGCCACAGTATCTCAG

CTCAGAGGCTGCTGAGGGACAGGGCACTCTTCCCCGCCGTCCACACA<u>ATG</u>AGTGTTGGCCGGAG
GAAGCTGGCCCTGCTCTGGGCCCTGGCTCTCGCTCTGGCCTGCACCCGGCATACAGCCATGCCC
AGGATGGCTCCTCCGAATCCAGCTACAAGCACCACCCTGCCCTCTCTGCCTATCGCCCGGGGC
CCAGCGGGGTCCCGCTCCGTGGGGCGACTGTCTTCCCATCTCTGAGGACCATCCCTGTGGTACG
AGCCTCCAACCCGGCGCACAACGGGCGGGTGTGCAGCACCTGGGGCAGCTTCCACTACAAGACC
TTCGACGGCGACGTCTTCCGCTTCCCCGGCCTCTGCAACTACGTGTTCTCCGAGCACTGCGGTG
CCGCCTACGAGGATTTTAACATCCAGCTACGCCGCAGCCAGGAGTCAGCGGCCCCACGCTGAG
CAGGGTCCTCATGAAGGTGGATGGCGTGGTCATCCAGCTGACCAAGGGCTCCGTCCTGGTCAAC
GGCCACCCGGTCCTGCTGCCCTTCAGCCAGTCTGGGGTCCTCATTCAGCAGAGCAGCAGCTACA
CCAAGGTGGAGGCCAGGCTGGGCCTTGTCCTCATGTGGAACCACGATGACAGCCTGCTGCTGGA
GCTGGACACCAAATACGCCAACAAGACCTGTGGGCTCTGTGGGACTTCAACGGGATGCCCGTG
GTCAGGGAGCTCCTCTCCCACAACACCAAGCTGACACCCATGGAATTCGGGAACCTGCAGAAGA
TGGACGACCCCACGGAGCAGTGTCAGGACCCTGTCCCTGAACCCCGAGGAACTGCTCCACTGG
CTTTGGCATCTGTGAGGAGCTCCTGCACGGCCAGCTGTTCTCTGGCTGCGTGGCCCTGGTGGAC
GTCGGCAGCTACCTGGAGGCTTGCAGGCAAGACCTCTGCTTCTGTGAAGACACCGACCTGCTCA
GCTGCGTCTGCCACACCCTTGCCGAGTACTCCCGGCAGTGCACCCATGCAGGGGGGTTGCCCCA
GGACTGGCGGGGCCCTGACTTCTGCCCCCAGAAGTGCCCCAACAACATGCAGTACCACGAGTGC
CGCTCCCCCTGTGCAGACACCTGCTCCAACCAGGAGCACTCCCGGGCCTGTGAGGACCACTGTG
TGGCCGGCTGCTTCTGCCCTGAGGGGACGGTGCTTGACGACATCGGCCAGACCGGCTGTGTCCC
TGTGTCAAAGTGTGCCTGCGTCTACAACGGGGCTGCCTATGCCCCAGGGGCCACCTACTCCACA
GACTGCACCAACTGCACCTGCTCCGGAGGCCGGTGGAGCTGCCAGGAGGTTCCATGCCCGGGTA
CCTGCTCTGTGCTTGGAGGTGCCCACTTCTCAACGTTTGACGGGAAGCAATACACGGTGCACGG
CGACTGCAGCTATGTGCTGACCAAGCCCTGTGACAGCAGTGCCTTCACTGTACTGGCTGAGCTG
CGCAGGTGCGGGCTGACGGACAGCGAGACCTGCCTGAAGAGCGTGACACTGAGCCTGGATGGGG
CGCAGACGGTGGTGGTGATCAAGGCCAGTGGGGAAGTGTTCCTGAACCAGATCTACACCCAGCT
GCCCATCTCTGCAGCCAACGTCACCATCTTCAGACCCTCAACCTTCTTCATCATCGCCCAGACC
AGCCTGGGCCTGCAGCTGAACCTGCAGCTGGTGCCCACCATGCAGCTGTTCATGCAGCTGGCGC
CCAAGCTCCGTGGGCAGACCTGCGGTCTCTGTGGGAACTTCAACAGCATCCAGGCCGATGACTT
CCGGACCCTCAGTGGGGTGGTGGAGGCCACCGCTGCGGCCTTCTTCAACACCTTCAAGACCCAG

FIG._5A

```
GCCGCCTGCCCCAACATCAGGAACAGCTTCGAGGACCCCTGCTCTCTGAGCGTGGAGAATGAGA
AGTATGCTCAGCACTGGTGCTCGCAGCTGACCGATGCCGACGGCCCCTTCGGCCGGTGCCATGC
TGCCGTGAAGCCGGGCACCTACTACTCGAACTGCATGTTTGACACCTGCAACTGTGAGCGGAGC
GAGGACTGCCTTGTGCGCCGCGCTGTCCTCCTACGTGCACGCCTGTGCGCCAAGGGCGTGCAGC
TCGGCGGCTGGAGGGACGGCGTCTGCACGAAGCCTATGATCACTTGCCCCAAGTCAATGACGTA
CCACTACCATGTCAGCGCCTGCCAGCCCACCTGCCGCTCCCTGAGCGAGGGGACATCACCTGC
AGTGTTGGCTTCATCCCCGTGGATGGCTGCATCTGTCCCAAGGGCACCTTCCTGGACGACACGG
GCAAGTGTGTGCAGGCCAGCAACTGTCCCTGCTACCACAGAGGCTCCATGATCCCCAATGGGGA
GTCGGTGCACGACAGCGGGGCTATCTGCACCTGCACACATGGGAAGCTGAGCTGCATCGGAGGC
CAAGCCCCCGCCCCAGTGTGTGCTGCGCCCATGGTGTTCTTTGACTGCCGAAATGCCACGCCCA
GGGGCACAGGGGCTGGCTGTCAGAAGAGCTGCCACACACTGGACATGACCTGTTACAGCCCCCA
GTGTGTGCCTGGCTGCGTGTGCCCCGACGGGCTGGTGGCGGACGGCGAGGGCGGCTGCATCACT
GCGGAGGACTGCCCCTGCGTGCACAATAAGGCCAGCTACCGGGCCGGCCAGACCATCCGGGTGG
GCTGCAACACCTGCACCTGTGACAGCAGGATGTGGCGGTGCACAGATGACCCCTGCCTGGCCAC
CTGCGCCGTGTACGGGGACGGCCACTACCTCACCTTCGACGGACAGAGCTACAGCTTCAACGGA
GACTGCGAGTACACGCTGGTGCAGAACCACTGTGGCGGGAAGACAGCACCCAGGACTCCTTTC
GTGTTGTCACCGAGAACGTCCCCTGCGGCACCACAGGGACCACCTGCTCCAAGGCCATCAAGAT
TTTCCTGGGGGGCTTCGAGCTGAAGCTAAGCCATAGGAAGGTGGAGGTGATCGGGACGGACGAG
AGCCAGGAGGTGCCATACACCATCCGGCAGATGGGCATCTACCTGGTGGTGGACACCGACATTG
GCCTGGTGCTGCTGTGGGACAAGAAGACCAGCATCTTCATCAACCTCAGCCCCGAGTTCAAGGG
CAGGGTCTGCGGCCTGTGTGGAACTTCGACGACATCGCCGTTAATGACTTTGCCACGCGGAGC
CGGTCTGTGGTGGGGGACGTGCTGGAGTTTGGGAACAGCTGGAAGCTCTCCCCCTCCTGCCCAG
ATGCCCTGGCGCCCAAGGACCCCTGCACGGCCAACCCCTTCCGCAAGTCCTGGGCCCAGAAGCA
GTGCAGCATCCTCCACGGCCCCACCTTCGC   +3358
```

FIG._5B

COMPOSITIONS AND METHODS FOR THE INHIBITION OF MUC-5 MUCIN GENE EXPRESSION

CROSS REFERENCE TO RELATED APPLICATIONS

This application claims benefit under 35 USC §119(e) to the filing date of application Ser. No. 60/074,398, filed Feb. 11, 1998.

ACKNOWLEDGEMENTS

This invention was supported in part by grants from the Public Health Service (HL24136, HL43762). The U.S. Government may have rights in this invention.

INTRODUCTION

1. Technical Field

The present invention provides for methods of identifying compounds for treating medical conditions related to the inappropriate production of mucin, such as Pseudomonas infections of cystic fibrosis patients, bronchial pneumonia, chronic bronchitis and bronchial asthma.

2. Background

Mucins are a family of glycoproteins secreted from epithelial cells at many body surfaces, including the eyes, pancreatic ducts, gallbladder, prostate and mainly, respiratory, gastrointestinal and female reproductive tracts. Mucins are responsible for the viscoelastic properties of mucus. In the airways, mucin interacts with cilia to trap and clear pathogens and irritants. Bacterial infection of the airway epithelium is often accompanied by mucin overproduction. In addition, airway diseases such as chronic bronchitis, cystic fibrosis and asthma are characterized by mucus hypersecretion. Hypersecretion can overwhelm the ability of the cilia to function properly. Mucociliary impairment leads to airway mucus plugging which promotes chronic infection, airflow obstruction, and sometimes death.

Nine mucin genes are known to be expressed in man: MUC 1, MUC 2, MUC 3, MUC 4, MUC 5AC, MUC 5B, MUC 6, MUC 7 and MUC 8 (Bobek, et al. (1993) *J. Biol. Chem.* 268:20563–9; Dusseyn, et al., (1997), *J. Biol. Chem.* 272:3168–78; Gendler, et al. (1991) *Am. Rev.Resp. Dis.* 144:S42–S47; Gum, et al. (1989) *J. Biol. Chem.* 264:6480–6487; Gum, et al. (1990) *Biochemical and Biophysical Research Communications* 171:407–415; Lesuffleur, et al. (1995) *J. Biol. Chem.,* 270:13665–13673; Meerzaman, et al. (1994) *J. Biol. Chem.* 269:12932–12939; Porchet, et al. (1991) *Biochem. Biophys. Res. Comm.* 175 (2):414–422; Shankar, et al. (1994) *Biochem. J.,* 300:295–298; Toribara, et al. (1997) *J. Biol. Chem.* 272:16398–403). Cysteine-rich domains are considered to be typical of mucin sequences, having been reported in many mucins including MUC 2(Gum, et al. (1992), *J. Biol. Chem.* 267:21375–21383; Gum, et al. (1994), *J. Biol. Chem.* 269:2440–2446), MUC 5AC (Meerzaman, et al. (1994), *J. Biol. Chem.* 269:12932–12939), MUC 5B (Desseyn, et al. (1997) *J. Biol. Chem.* 272:3168–3178) and MUC 6 (Toribara, et al. (1997) *J. Biol. Chem.* 272:16398–16403) as well as in rat (Ohmori, et al. (1994) *J. Biol. Chem.* 269:17833–17840), pig (Eckhardt, et al. (1991) *The Journal of Biological Chemistry,* 266(15):9678–9686), cow (Bhargava, et al. (1990) *Proc. Nat. Acad. Sci. U.S.A.* 97:6798–6802) and frog (Probst, et al. (1990) *Biochemistry* 29:6240–6244) mucins. The cysteine-rich domains in mucins show varying degrees of similarity to the D-domains of von Willebrand factor (vWF).

Cystic fibrosis ("CF") commonly occurs among Caucasians (approximately 1 in 2,000 newborns). The mode of inheritance is autosomal recessive and about 5% of the normal population carries the defective gene. Affected individuals can generally live with reasonable lung function until the onset of a chronic bacterial infection. Almost all patients contract either *Pseudomonas aeruginosa* or *Staphylococcus aureus* infections. Mucus overproduction resulting from the bacterial infection damages lung function directly by plugging airways and indirectly by shielding the bacteria from endogenous and exogenous antibacterial agents. This creates a "wound that does not heal" and causes chronic influx of inflammatory cells whose proteases degrade gas exchange tissue. Respiratory function declines relentlessly until death results.

Current treatments fail to effect the complete eradication or prevention of these bacterial infections in cystic fibrosis patients nor do they ameliorate the overproduction of mucus. In addition, antimicrobial therapy using antibiotic therapeutic protocols have complications. Patients with CF dispose of antimicrobial agents more rapidly than do non-CF individuals, which results in the use of higher doses than those normally recommended. Strains of *Pseudomonas aeruginosa* ("PA") can dissociate into multiple serotypic forms, which often have different antimicrobial susceptibility patterns. Since PA infection is chronic and the infecting strains of *Pseudomonas aeruginosa* are rarely eradicated, resistance to multiple antimicrobial agents frequently develops, thwarting antibiotic therapies. Moreover, therapeutic levels of antimicrobial agents in sputum are difficult to achieve because of poor penetration and inactivation. Mucoid exopolysaccharides of mucoid PA strains additionally present a barrier to penetration of some antibiotics. Finally, allergy to certain antibiotics (such as betalactam) precludes antibiotic therapy with some patients. Thus, as it is virtually impossible to eradicate the bacteria, it is important to find alternate therapies to improve lung function and prolong life. The ability to control mucin production may provide an alternative route to prevent or alleviate airway plugging.

In addition to its role in exacerbating pulmonary infections in cystic fibrosis patients, mucin overproduction is also a debilitating feature of chronic bronchitis, bronchial pneumonia and chronic asthma. Smoking is the most important risk factor for chronic bronchitis. Individuals dying in status asthmaticus are always observed to have mucus-obstructed airways.

Consequently, there is a need to provide therapies for reducing mucus production in individuals suffering from airway diseases such as cystic fibrosis, chronic bronchitis, bronchial pneumonia and asthma.

RELEVANT LITERATURE

Recent work has suggested that MUC 4 and MUC 5AC are the most highly expressed mucins in the upper airway (Gendler, et al. (1996) *Pediatric Pulmonology* 13S:290 Abstract). Mucus secretions in the airway are produced from two different secretory cell populations, surface epithelial goblet cells and the mucous cells in the submucosal glands. MUC 5AC has been reported to be expressed primarily in the goblet cells (Hovenberg, et al. (1996) *Biochem. J.* 318:319–24).

Increased expression of some members of the mucin family in response to certain effectors has been reported. Recent reports have indicated that MUC 2, MUC 4 and MUC 5B are expressed at a higher level in the airways of cystic fibrosis patients compared with non-CF patients (Gendler et al. (1996) *Pediatric Pulmonology* 13S:290 Abstract); Li, et al. (1997) *Proc. Nat. Acad. Sci. (USA)* 94:967–972). Steiger et al. (1995) (*Am. J. Resp. Cell and Molec. Biol.* 12:307–314) have reported that bacterial endotoxin stimulates both the storage and release of a mucin-like molecule in airway epithelial cells. Levine, et al. (1995) (*Am. J. Resp. Dis.* 12:196–204) have reported an increase in the steady state levels of MUC 2 mRNA in NCI-H292 cells by exposure to tumor necrosis factor-$\alpha$. Li et al. (*Proc. Natl Acad. Sci.* (1997) 94:967–972) have reported that PA lipopolysaccharide ("LPS") can increase transcription of the MUC 2 gene in epithelial cells. Pre-incubation of the cells with the protein tyrosine kinase inhibitor Genistein abolished the increase in transcription. Recent work in the laboratory of some of the present inventors has suggested that MUC 5AC transcription is also increased after exposure to various Gram-negative and Gram-positive bacteria in both bronchial explants and cultured airway epithelial cells. Borchers and Leikauf have recently reported (*Am. J. Respir. Critical Care Med.* 155:A778 (1997)) that exposure of rats to acrolein, a low molecular weight aldehyde found in tobacco smoke, results in an increase in MUC-2 mRNA and concurrent secretion of mucin in airway tissue.

Partial MUC 5AC cDNA sequences have been reported (Meerzaman, et al. (1994) *J. Biol. Chem.*, 269:12932–12939); Guyonnet-Duperat, et al. (1995) *Biochem. J.* 211–209). The nucleotide sequence of human gastric mucin cDNA, HGM-1, from nucleotides 1942–2281 is 99% identical to the MUC 5AC clone JUL 32 (Guyonnet-Duperat, et al. (1995) *Biochem. J.* 211–209) and the sequence from nucleotides 2190–2541 is 92% identical to the 5' end of MUC 5AC clone NP3a (Klomp, et al. (1995) Biochem. J., 308:831–80). The sequence of the MUC 2 gene promoter has been reported (Velcich, et al. (1997) *J. Biol. Chem.* 272:7968–7976 (1997).

SUMMARY OF THE INVENTION

The present invention provides methods and compositions for the selection of inhibitors of mucin production. The present inventors have identified for the first time the regulatory elements of the human MUC 5AC gene which control the response of the gene to effectors which induce the expression of MUC 5AC. Nucleotide sequence of the regulatory region is provided herein. By using these regulatory elements, particularly in combination with a readily detectable reporter gene, it is possible to identify compounds that inhibit the induction of mucin genes, particularly MUC 5AC, by various effectors, or mucomones. Inhibitor compounds thus identified are useful in therapeutic methods for the treatment of diseases and conditions associated with the inappropriate production of mucin.

The present inventors have additionally discovered that tobacco smoke, in the form of smoke-conditioned culture medium, can serve as a mucomone to induce the transcription of mucin genes, in particular, the MUC 5AC gene. Nucleotide sequences important for providing induction of MUC 5AC by tobacco smoke are identified.

The present invention thus provides polynucleotide molecules comprising one or more MUC 5AC mucomone response elements, mucomone-inducible reporter gene constructs comprising the MUC 5AC mucomone response elements operably linked to a reporter gene, and cells comprising the reporter gene constructs.

The present invention additionally provides methods for identifying compounds that inhibit mucin production using the polynucleotide molecules, reporter gene constructs and cells of the present invention. In one embodiment, the method of the present invention comprises contacting cells comprising a mucomone-inducible reporter gene construct with a test compound, contacting said cells with a mucomone, and determining the difference in reporter gene activity in response to mucomone in the presence and absence of the test compound. The method is particularly useful for identifying compounds that inhibit tobacco smoke-induced mucin production.

Mucomone-induced mucin production can be affected in a variety of ways, for example, by inhibiting binding of mucomones to an epithelial cell or by inhibiting any crucial step in the signal transduction cascade between binding of a mucomone and mucin gene activation, including inhibiting transcription factors that interact with mucin promoters. Such inhibitors can be used in treatments of medical conditions related to the inappropriate expression of mucin, such as, for example, cystic fibrosis, chronic bronchitis, bronchial pneumonia and bronchial asthma. The invention includes methods and compositions related to drug discovery and therapeutic treatments.

Another embodiment of the invention provides for methods for treating an animal by inhibiting the production of mucin in epithelial cells, particularly airway epithelial cells, by administering an effective amount of an inhibitor of mucomone-induced mucin production to the animal. Other methods, compounds and compositions are more fully described herein.

BRIEF DESCRIPTION OF THE DRAWINGS

FIGS. 1A and 1B show the DNA sequence of the 5' regulatory region of the human MUC 5AC gene (SEQ ID No: 1), from –3752 bp to +83 bp, +1 bp being the transcription start site. The transcription start site and the translation start sites (ATG) are underlined.

FIG. 2 is a bar graph showing the dose-dependent and time-dependent response of M4-2 transfected HM3 cells to environmental tobacco smoke (ETS)—exposed medium. The duration of exposure to the ETS medium is shown in hours on the horizontal axis. Relative luciferase activity is shown on the vertical axis.

FIG. 3 is a bar graph showing the dose-dependent and time-dependent response of M4-2 transfected NCIH292 cells to environmental tobacco smoke (ETS)—exposed medium. The duration of exposure to the ETS medium is shown in hours on the horizontal axis. Relative luciferase activity is shown on the vertical axis.

FIG. 4 is a bar graph showing effect of various inhibitors on the RLA induced by exposure to the ETS—medium.

FIGS. 5A and 5B show the nucleotide sequence of the MUC 5AC cDNA (SEQ ID No. 2).

FIG. 6 shows the nucleotide sequence of a MUC 5AC genomic clone from –16 bp to +412 bp (SEQ ID No:22). The transcription start site is designated +1 bp and is underlined. The first exon is shown in bold. The putative translation start ATG is underlined. An intron-exon junction occurs between +136 and +137.

DESCRIPTION OF SPECIFIC EMBODIMENTS

DEFINITIONS

Mucin or mucins typically refer to the structural protein components of mucus from epithelial cells that protect tissues, such as the respiratory and reproductive tracts.

Typically, mucins form extremely large oligomers through linkage of glycoprotein monomers using disulfide bonds. Usually, such glycoproteins are large >100,000 daltons and typically consist of approximately 75% carbohydrate and 25% protein. Mucins include proteins encoded by the MUC genes described herein. Altered mucins, which contain abnormal concentration of sulfate, sialic acid or fucose, also occur in pathological conditions, such as inflammatory diseases.

Mucomones refer to molecules that induce or effect, directly or indirectly, mucin production and typically include proteins, amino acids, simple sugars, complex sugars, lipopolysaccharides ("LPS") and other pathogen exoproducts, irritants like tobacco smoke and constituents of smoke such as acrolein.

By mucomone-induced mucin production is meant an increase in mucin production in a cell in response to the presence of a mucomone. In some instances, a reporter gene will be substituted for a mucin gene and in these cases mucomone-induced mucin production can be determined with reference to the increase in reporter gene activity in response to the presence of a mucomone.

By reporter gene activity is meant any activity associated with expression of the reporter gene including the transcription or translation of the gene or the presence or activity of the gene product.

Production, when used in the context of describing a cellular process, typically refers to a cellular process or processes involved in maintaining the steady state level of a molecule, such as a mucin, for example MUC 5AC. Consequently, production includes the cellular processes of gene activation or induction, transcription, protein synthesis, and in appropriate instances, protein modification and/or secretion. Production also refers to cellular and extracellular processes responsible for maintaining steady state levels of a molecule, such degradation pathways and extracellular structural elements that anchor molecules to cells or in an extracellular matrix.

Secretion, when used in the context of describing a cellular process, typically refers to a cellular process or processes of transporting a molecule from inside the cell to an extracellular location.

By operably linked, as used herein in the context of assembly of the reporter gene construct, is meant that the component sequences are joined in such fashion that they function together to achieve the intended purpose. For example, a mucomone response element is operably linked to a responsive promoter when the promoter is activated in response to the effector (mucomone) to which the mucomone response element responds. A reporter gene is operably linked to a promoter when transcription of the reporter gene from the promoter can occur.

Protein synthesis, when used in the context of describing a cellular process, typically refers to a cellular process or processes involved in making a molecule, such as a mucin, for example MUC 5AC. Protein synthesis may involve transport of the molecule within the cell making the molecule. The term protein synthesis, however, does not include reference to the term secretion described herein.

Transcriptional control element refers to a nucleotide sequence which is involved in the regulation of transcription of a gene or genes. Transcriptional control elements include mucomone response elements, promoters, enhancers, and the like.

Mucomone response element refers to a nucleotide sequence which, when operably linked to a responsive promoter, results in the activation of transcription from the promoter in response to a mucomone. A responsive promoter is one that is capable of activation by a mucomone response element. Activation of transcription includes either initiation of transcription or increase in the rate or amount of transcription.

Treatment of a disease or condition refers to procedures for the amelioration or eradication of a disease or condition, or of symptoms associated with a disease or condition, and includes the prevention of the development of such disease or condition or of symptoms associated with such disease or condition.

DESCRIPTION OF EMBODIMENTS

Overproduction of mucins has been implicated as a factor in a number of diseases or conditions of the airway including chronic bronchitis, bronchial pneumonia, asthma and bacterial infections associated with cystic fibrosis. Exposure of airway cells to various external stimulants, such as *Pseudomonas aeruginosa* lipopolysaccharides, has been shown to result in increased mucin production. Recent reports suggest that MUC 5AC is one of the most highly expressed mucins in the upper airway and is expressed primarily in goblet cells.

The present inventors have for the first time isolated and sequenced the 5' regulatory region of the human MUC 5AC gene. Mucomone response elements have been identified within the 5' regulatory region which are responsible for the increase in transcription of the MUC 5AC gene, and consequent increase in mucin production, in vivo, in response to certain effectors, herein called mucomones. The MUC 5AC mucomone response elements, in combination with a responsive promoter, can effect an increase in activity of an associated gene in response to the presence of a mucomone. A mucomone-inducible reporter gene construct can be prepared in which reporter gene activity is induced by the presence of mucomone. Such constructs are useful in a method for the identification of compounds that inhibit mucomone-induced mucin production. Inhibitor compounds that are identified are useful in a method for inhibiting mucin production in animals.

The 5' regulatory region of the human MUC 5AC gene, including one or more mucomone response elements, is present on an approximately 4 kilobase pair ("4 KB") DNA fragment which is immediately adjacent to, and upstream from, the MUC 5AC transcription initiation site. This 4 KB fragment has now been identified, isolated and sequenced. A vector containing the cloned 4KB fragment was deposited under the terms of the Budapest Treaty with the American Type Culture Collection, 10801 University Blvd., Manassas, Va. 20110 as ATCC 98701 on Mar. 26, 1998. Nucleotide sequence of 3753 nucleotides from the region of the 4 KB fragment immediately adjacent to the transcription initiation site is provided in FIG. 1A and B (SEQ ID No. 1). The 4 KB fragment contains one or more mucomone response elements that are responsible for the increase in MUC 5AC transcriptional activity in the presence of a mucomone, particularly environmental tobacco smoke or *P. aeruginosa*-conditioned medium. The 4 KB MUC 5AC 5' regulatory region fragment is readily identified and isolated using the information disclosed herein by methods that are well-known in the art. For example, the 4KB fragment may be identified by hybridization of a human genomic library with a DNA fragment probe comprising at least 20 consecutive nucleotides, preferably 50 consecutive nucleotides, more preferably 100 consecutive nucleotides of the sequence of FIG. 1A and B (SEQ ID No. 1), or the complement of that sequence. The DNA fragment probe is conveniently prepared by methods that are well known in the art, for example by chemical synthesis. Preparation of a human genome library and screening for clones containing the 4 KB MUC 5AC 5' regulatory region fragment by hybridization can be carried out by well known methods, for example, as described in Sambrook et al. (*Molecular Cloning,* Cold Spring Harbor Laboratories 1989). Alternatively, a DNA fragment comprising the sequence of the 4 KB MUC 5AC 5' regulatory region, or fragments thereof, may be synthesized using the polymerase chain reaction using primers based on the sequence disclosed herein for this region and the complement of that sequence. Methods for designing primers for amplification of particular sequences, as well as the PCR protocols, are well known in the art, see for example, *PCR Protocols: A Guide to Methods and Applications,* Innis et al., eds., Academic Press, 1990. The entire 4 KB fragment, or a portion thereof comprising at least one mucomone response element, is operably linked to a reporter gene by conventional molecular biological methods to provide the mucomone-inducible reporter gene constructs of the present invention.

The present invention includes an isolated polynucleotide molecule comprising at least 20 consecutive nucleotides, preferably at least 50 consecutive nucleotides, most preferably at least 100 or more consecutive nucleotides, of the 4 KB MUC 5AC 5' regulatory region (SEQ ID No:1) or a complement of that sequence. The nucleotide sequence of 3753 bases of the MUC 5AC 5' regulatory region immediately upstream of the MUC 5AC transcription initiation site is shown in FIG. 1A and B(SEQ ID No. 1). The MUC 5AC transcription initiation site is underlined and is designated as nucleotide +1. The 5' regulatory region is numbered counting backward from the transcription initiation site (that is, from right to left) from –1 bp to –3752 bp. A TATA box is present at –28 through –31. Thus, the 4 KB MUC 5AC 5' regulatory region fragment shown in FIG. 1A and B contains the MUC 5AC promoter. FIG. 5 shows 3358 nucleotides of the sequence of a MUC 5AC cDNA (SEQ ID No. 2) beginning with the transcription initiation site. The transcription initiation site is again designated as nucleotide +1. The cDNA sequence is numbered counting forward (that is, left to right) from +1 to +3358. The ATG translational start codon is underlined. FIG. 6 shows the genomic sequence of MUC 5AC from just before the transcription initiation site (–16 bp) through the first exon into the first intron (+412).

The polynucleotide molecule of the present invention is useful as a DNA fragment probe for identification and isolation of the 4 KB MUC 5AC 5' regulatory region. The polynucleotide molecule of the present invention may also be operably linked to a reporter gene to provide a mucomone-inducible reporter gene construct. The polynucleotide molecule of the present invention may include the entire 4 KB MUC 5AC 5' regulatory region fragment, or portions thereof comprising at least 20 consecutive nucleotides, preferably 50 consecutive nucleotides, more preferably 100 or more consecutive nucleotides of the nucleotide sequence of FIG. 1A and B (SEQ ID No. 1). For use in combination with a reporter gene, the polynucleotide molecule chosen will preferably contain one or more mucomone response elements. The polynucleotide molecule can be prepared in any of a number of ways that are well known in the art, for example by chemical or enzymatic synthesis (for example, PCR). The polynucleotide molecule may be prepared by fragmentation of larger DNA fragments (for example, the 4 KB MUC 5AC 5' regulatory region fragment), for example, by restriction digestion or digestion with other endonucleases or exonucleases or by mechanical shearing.

From the disclosure of the sequence of the 5' regulatory region of the MUC 5AC gene now provided, a mucomone response element can be identified by methods that are well-known in the art or by methods described herein. In general, a first reporter gene construct can be made comprising a sequence of at least 20 consecutive nucleotides of the 4 KB MUC 5AC 5' regulatory region fragment operably linked to a responsive promoter, for example the MUC 5AC promoter as identified herein, and the coding region of a reporter gene. The first reporter gene construct will preferably comprise DNA fragments having the sequence of at least 20 consecutive nucleotides, preferably 50 consecutive nucleotides, more preferably 100–200 consecutive nucleotides, most preferably 500 or more consecutive nucleotides, of the 4 KB MUC 5AC 5' regulatory region (SEQ ID No:1). Reporter gene activity in response to the presence of a mucomone can be determined by any of a variety of methods as described herein. For comparison, the response of a control reporter gene construct is determined. The control reporter gene construct is similar to the first reporter gene construct but does not contain sequences from the 4 KB MUC 5AC 5' regulatory region but may contain the MUC 5AC promoter. When the relative reporter gene activity in response to mucomone of the first reporter gene construct is at least two-fold greater than that of the control reporter gene construct, a mucomone response element is present in the first reporter gene construct.

A mucomone response element may respond to a variety of different mucomones or may be specific for particular mucomone or a limited group of mucomones. A mucomone response element may respond differently to different mucomones. Preferably, in identifying a mucomone response element for use in the method of the present invention to identify inhibitors of mucomone-induced mucin production, the response element will be selected for response to the particular mucomone or mucomones to be employed in the method to identify inhibitor compounds.

A mucomone response element can be operably linked to a responsive promoter and a reporter gene to provide the mucomone-inducible reporter gene construct of the present invention. By mucomone-inducible is intended an increase in reporter gene activity in response to the presence of a mucomone. It will be apparent that the increase in reporter gene activity in response to a mucomone can be observed only if the construct is present in a cell which is capable of mucomone-induced mucin production.

A cell is capable of mucomone-induced mucin production if it contains the components necessary to provide increased transcriptional activity of a mucin gene or genes in response to the presence of a mucomone. Typically, cells of the type which produce mucin in vivo, particularly those cells which produce MUC 5AC protein in vivo, will be capable of mucomone induced mucin production. In particular, certain epithelial cells or cell lines are capable of mucomone-induced mucin production and are useful in the practice of the present invention.

The mucomone-inducible reporter gene construct of the present invention is useful in a method for identifying an inhibitor of mucomone-induced mucin production. In one embodiment, the method of the present invention comprises the steps of (a) contacting cells comprising a mucomone-inducible reporter gene construct with a mucomone, wherein said reporter gene construct comprises a mucomone response element comprising at least 20 consecutive nucleotides of the 4 KB MUC 5AC 5' regulatory region (SEQ ID No:1) and a responsive promoter, operably linked to a reporter gene, (b) contacting said cells with a test compound, and comparing the reporter gene activity after performing steps (a) and (b) with the reporter gene activity after performing only step (a).

The present invention recognizes that epithelial cells involved in mucin production would be useful components of in vitro methods for identifying compounds that are useful as therapeutics, such as compounds that inhibit mucomone-induced mucin production. Although not essential for practicing the invention, such identifying methods can involve screening assay systems that permit high throughput automated screening.

Such methods include the use of mucomones that can induce mucin production in the cell type employed in the method. Examples of such mucomones include, but are not limited to, bacterial conditioned medium from both Gram-negative and Gram-positive bacteria, including PA conditioned media, E. coli conditioned media, LPS from PA, E. coli and other Gram-negative bacteria, Lipid A from PA, E. coli and other Gram-negative bacteria, irritants such as tobacco smoke and constituents of smoke such as acrolein, as well as smoke-exposed culture medium, and other mucomones known in the art or described herein. The preparation of bacterial conditioned medium is well known in the art (See, for example, Li et al. 1997, supra) and can be readily made by growing a bacterial culture in an appropriate culture medium, removing the bacteria after a suitable time by, for instance centrifugation, and removing any residual viable bacteria from the culture medium by, for example, ultrafiltration. Mucomones that are particularly useful in the practice of the present invention include conditioned growth medium from any Gram-negative or Gram-positive bacteria, or specific components thereof such as LPS; environmental tobacco smoke-conditioned medium, or specific components thereof; IL1, TNF-α, other inflammatory mediators, forskolin, TPA, dibutryl cAMP, ceramide. Preferred mucomones include bacterial LPS, smoke-conditioned medium and bacterial conditioned medium.

Typically, in the method of the present invention, mucomone will be added to cells after exposure of the cells to a test compound but may be added simultaneously with the test compound or may be added prior to the addition of test compound. It is within the competence of one of ordinary skill in the art to determine the preferred order of addition for any particular combination of mucomone and test compound. Likewise, the manner of addition and the amount of mucomone added will vary with the particular mucomone and are readily determinable by one of ordinary skill in the art.

The method of the present invention can be used to screen any of a number of compounds for the ability to inhibit mucomone-induced mucin production, including, but not limited to, tyrosine kinase inhibitors, protein kinase A inhibitors, mitogen-activated protein (MAP) kinase inhibitors, inhibitors of mucomone binding, and other types of compounds.

A number of methods may be used to detect mucin production or mucin gene activation, indirectly or directly. For instance, mucin production can be directly detected by measuring mucin protein synthesis or by measuring mucin in cell supernatants or airway lavage fluid, and mucin gene activation can be directly detected by measuring transcription or RNA levels using the appropriate labels or probes for such assays. For example, an RNase protection assay (RPA), as described herein and known in the art, can be used to study the effect of a compound on the transcriptional activity of a MUC gene by detecting changes in the RNA levels of one or more of the known mucin genes (Gendler, et al. (1990) J. Biol. Chem. 265:15286–15293; Gum, et al. (1994) J. Biol. Chem. 269:2440–2446; Velcich, et al. (1997) J. Biol. Chem. 272:7968–7976); Gum, et al. (1990) Biochemical and Biophysical Research Communications 171:407–415; Aubert et, al. (1991) American Journal of Respiratory Cell and Molecular Biology 5:175–185; Rose, et al. (1989) J. Biol. Chem 264:8193–99; Toribara, et al. (1993) J. Biol. Chem. 268:5879–5885; Reddy, M. S. (1992) Biochemical J. 287:639–43; Sachdev (1994) Biochemical J. 300 (pt 2):295–298). Mucin probes can be selected from among the known nucleotide sequences for mucin, such as for human mucins, and can be used for RPA or traditional hybridization techniques, such as, for example, Northern blots. Preferably, probes specific for MUC 5AC are used. Oligonucleotides comprising known mucin nucleotide sequences can also be used to measure RNA levels by quantitative PCR. The methods and sequences of the above-referenced publications are herein incorporated by reference. Direct detection methods may also include antibody assays for mucins to assess regulation at the protein level, such as the use of A10G5 monoclonal antibody to detect MUC-2 (Finkbeiner, et al. (1988) Am. J Pathol. 131:290–297). Monoclonal or polyclonal antibodies to MUC 5AC may be prepared by methods that are well known in the art. It should be remembered that mucin secretion is not a desirable method for detecting mucin production because mucin secretion from the cells, especially mucin secretion within 2–3 hours in response to a mucomone, is not indicative of gene upregulation. Such rapid secretion measurements provide a better measurement of release of stored mucin from the cell and not synthesis of a large molecule comprised both of protein and sugar, which often has a total molecular weight of 1,000,000 daltons.

Conveniently, a reporter gene assay can be used to indirectly determine the amount of mucomone-induced mucin production. An increase in reporter gene activity in response to mucomone is indicative of mucomone-induced mucin production. As will be readily apparent, such an assay can also be used to determine the inhibition of mucomone-induced mucin production by various inhibitors. The assay is typically carried out using an epithelial cell comprising a mucomone-inducible reporter gene construct as described herein. Reporter gene activity is determined by methods appropriate for the particular reporter gene chosen. For example, where the reporter gene construct contains a luciferase gene or a chloramphenicol acetyltransferase gene as the reporter gene, luciferase or chloramphenicol acetyltransferase (CAT) assays, respectively, can be used to determine the amount of mucomone-induced reporter gene activity and the inhibition of that mucomone-induced activity in the presence of a test compound.

A reporter gene includes any gene that expresses a detectable gene product, which may be RNA or protein. Preferred reporter genes are those whose gene products are readily detectable. The reporter gene may also be included in the construct in the form of a fusion with a gene that includes desired transcriptional regulatory sequences or exhibits other desirable properties. For example, reporter gene fusion with a mucin gene may be used. Many reporter genes and transcriptional regulatory elements are known to those of skill in the art and others may be identified or synthesized by methods known to those of skill in the art.

Examples of useful reporter genes include, but are not limited to CAT (chloramphenicol acetyl transferase) (Alton and Vapnek (1979) *Nature* 282:864–869), luciferase, and other readily detectable enzyme systems, such as beta-galactosidase, firefly luciferase (deWet, et al. (1987) *Mol. Cell. Biol.* 7:725–737); bacterial luciferase (Engebrecht and Silverman (1984), *PNAS* 1:4154–4158; Baldwin, et al. (1984) *Biochemistry* 23:3663–3667), alkaline phosphatase (Toh, et al. (1989) *Eur. J. Biochem.* 182:231–238, Hall et al. (1983) *J. Mol. Appl. Gen.* 2:101), and GFP (green fluorescent protein) (Chalfie, et al. (1994) *Science* 263:802–805).

The mucomone-inducible reporter gene construct is assembled by methods that are well known in the art. The assembly is most conveniently accomplished by ligation of DNA fragments, for instance restriction fragments or chemically or enzymatically synthesized DNA fragments. Alternatively, the various DNA sequences may be chemically or enzymatically synthesized as a single fragment. Expression of the reporter gene can be monitored in any of a number of ways that are well known in the art including, for example, by measuring transcription or translation of the reporter gene or the presence or activity of the reporter gene product.

Mucomone-inducible reporter gene constructs can be prepared by operably linking a reporter gene or reporter gene coding region with a portion of the 4KB 5' regulatory region fragment of the MUC 5AC gene containing one or more mucomone response elements and a responsive promoter. Typically, the portion of the 4 KB 5' regulatory region chosen will also contain the MUC 5AC promoter. Alternatively, the MUC 5AC promoter may be joined to a portion of the 4 KB MUC 5AC regulatory region that is not adjacent to the MUC 5AC promoter in the native sequence. For example, a portion of the 4KB MUC 5AC regulatory region from −3752 bp to −3555 bp of the sequence of FIG. 1A and B may be joined directly to a fragment containing the promoter, for instance, the portion from −50 bp to +1 bp. Other promoters, for example, a MUC 2 promoter or a thymidine kinase promoter, may be used in place of, or in addition, to the MUC 5AC promoter, provided that the particular promoter chosen is responsive to the mucomone response elements. Preferably, the reporter gene construct includes the MUC 5AC promoter and at least one mucomone response element from the 4 KB MUC 5AC 5' regulatory region. For example, the reporter gene construct will include a mucomone response element contained within the polynucleotide molecule having the nucleotide sequence of FIG. 1A and B (SEQ ID No:1) and identified by the procedure already described. Any portion of the 4 KB MUC 5AC 5' regulatory region, up to the entire 4 KB fragment (that is, from −3752 bp to −1 bp of the sequence of FIG. 1A and B, which corresponds to nucleotides 1–3753 of SEQ ID No:1), that contains one or more mucomone response elements may be used in making the reporter gene construct. The polynucleotide molecules containing the mucomone response elements can be operably linked to the MUC 5AC promoter or to another responsive promoter, such as, for example, the thymidine kinase (tk) promoter, to render such heterologous promoters responsive to mucomone stimulation. The reporter gene constructs will demonstrate at least a 2-fold increase in reporter gene activity, preferably a 5-fold increase or greater, more preferably a 10-fold increase or greater and most preferably a 50-fold increase or greater in response to mucomone.

The mucomone-inducible reporter gene construct may contain additional transcriptional regulatory elements or other sequences, that are not necessarily regulated by the mucomone or the mucomone receptor, but are selected for their ability to reduce background level transcription or to amplify the transduced signal and to thereby increase the sensitivity and reliability of the assay. In addition, sequences useful for transfection and selection of transfectants may be included. For example, selectable marker genes such as a gene for neomycin resistance or for G418 resistance, or sequences that provide homology with a host target sequence for homologous recombination of the vector into the host sequence can be present in the reporter gene construct.

Any cell, particularly an epithelial cell, that produces mucin in response to a mucomone can be used as a component of the assays described herein. Although most epithelial cells will exhibit mucomone inducible mucin production, the regulation of mucin production can vary from tissue to tissue as well as depend on the type of mucomone. Thus, if an inhibitor of colon or airway mucin production is desired, it will often be preferable to use colon or airway derived mucin producing cells in identifying such an inhibitor. If it is not known whether a cell produces mucin in response to a mucomone, mucomone-induced mucin production can be easily determined using the assay described herein. In brief, the cell is contacted with a mucomone and mucin production is measured before and after exposure of the cell to mucomone. Mucin production can be measured by any of the methods described herein and any other methods known in the art. Cells that are identified as producing mucin in response to mucomone in such assays can then be used in a method for identifying therapeutic compounds. Choice of cells is not restricted to this manner of selection and it will often be the case that some cell lines will be preferred irrespective of the tissue source, such as HM3 and NCIH929. Preferred cells for the practice of the present invention are those that respond well to mucomones, are convenient to culture, and produce large reporter gene signals in the presence of a mucomone compared to in the absence of a mucomone, i.e. cells that have a low level of mucin production in the absence of a mucomone. Preferably, NCIH292, HM3, Hela, CFTE290, NCIH292 and 16Lu cells are used in the identification methods and most preferably HM3 and NCIH292 are used. Cells from a variety of epithelial tissues can be used as well, such as airway secretory cells, ciliated cells, epithelial cells of the respiratory tract, kidney secretory cells and reproductive tract epithelial cells. Once a particular cell type has been selected, various direct and indirect detection assays of mucin production can be used, as described herein.

For use in the method of the present invention, the cells are transfected with a reporter gene construct by any of a number of methods that are well known in the art, for example as described in Felgner, et al. *Proc. Natl Acad. Sci.* 84:7413 (1987), Wigler, et al. (1977) *Cell* 11:233, Neumann, et al. (1982) *EMBO J.* 1:841–845, Sussman, et al. (1984) *Mol. Cell. Biol.* 4:1641. The reporter gene construct may be transiently present in the cell or may be stably incorporated into the chromosome of the cell. Preferably, the reporter gene construct is stably incorporated into the chromosome.

In the method of the present invention, a test compound can be assayed for its ability to inhibit mucomone-induced mucin production in cells comprising a mucomone-inducible reporter gene construct by measuring a change in reporter gene activity in the presence and absence (control) of the compound being tested. It will be recognized that such controls can be used in any of the assays described herein and that other controls can be readily interchanged to achieve specific detection, such as using cells without functional 5' regulatory regions of the mucin gene operably linked to a functional reporter gene, by not adding a mucomone or by blocking the action of an added inhibitor. The method is typically carried out using an epithelial cell line in which a mucomone-inducible reporter gene construct is stably incorporated into the chromosome. The method may alternatively be carried out using cells that are transiently transfected with the reporter gene construct. The cells comprising the reporter gene construct are contacted with mucomone to activate the mucomone-induced reporter gene construct. The cells are additionally contacted with the compound to be tested. The cells may be exposed to the mucomone prior to addition of the test compound, simultaneously with the addition of the test compound or at some time after the addition of the test compound. Reporter gene activity in response to mucomone is measured after exposure to the test compound and compared with reporter gene activity in the absence of the test compound by methods described herein. It will be apparent that mucomone-induced reporter gene activity may be optimized by varying assay parameters, such as concentration of mucomone used, timing of addition of mucomone, etc. Optimization of mucomone-induced reporter gene activity is well within the competence of one of ordinary skill in the art and is best accomplished in separate assays prior to addition of test compounds. It will also be apparent that the test compound may be used in a range of concentrations to optimize the effect on mucomone-induced reporter gene activity.

The method of the present invention is typically carried out as follows. Cells capable of mucomone-induced mucin production are transfected with a mucomone-inducible reporter gene construct by standard procedures (for example, see Hiro et al. *J. Cell. Biochem.* (1996) 61:350–362). The cells are incubated under standard conditions following transfection. Approximately 40 hours after transfection, the test compound is added to the cells. After exposure of the transfected cells to the test compound for about two hours, a mucomone is added and incubation is continued for approximately an additional 6 to 24 hours. The cells are then harvested and the activity of the reporter gene is determined for the test sample. A control sample is prepared identically except that no test compound is added at 40 hours. The amount of reporter gene activity in the test sample is compared with that of the control sample. The reporter gene activity may be normalized to some internal control, for example, total protein or the amount or activity of a constitutive cellular protein. Alternatively, the reporter gene construct may contain a second readily detectable gene, the activity of which can be used to normalize the reporter gene activity. When the amount of reporter gene activity in the control sample is greater than the amount of reporter gene activity in the test sample, an inhibitor of mucomone-induced mucin production has been identified. Preferably, the control reporter gene activity is at least two-fold greater than the test sample reporter gene activity.

In addition to the transfected cells of the present invention, transgenic animals comprising the mucomone-inducible reporter gene construct can be prepared. Methods of preparing transgenic animals are well known and include, for example, microinjection of a DNA molecule into the male pronucleus of a fertilized egg (Brinster et al. (1981) *Cell* 27:223; Costantini, et al. (1981) *Nature* 293:540), introduction of recombinant viral or retroviral molecules into an animal at a multi-cell stage, injection of a DNA molecule into an embryonic stem cell and transplantation into a blastocyst (WO 91/19796). Transgenic animals comprising the mucomone-inducible reporter gene construct can be used to identify inhibitors of mucomone-induced mucin production in vivo by evaluation of the reporter gene activation in response to mucomone in the presence and absence of the inhibitor compound. Preferred reporter genes for use in the transgenic animal of the present invention include β-galactosidase, human growth hormone and green fluorescent protein.

Any of a number of compound types can be tested for inhibition of mucomone-induced mucin production, including, but not limited to, inhibitors of mucomone binding, tyrosine kinase inhibitors, protein kinase A inhibitors, MAP kinase inhibitors, inhibitors of other components of the signal transduction pathway, inhibitors of transcription factors that interact with mucin promoters, and other compound types. Inhibitors of mucomone binding can include mucomone receptor antagonists such as, for example, LPS antagonists. Inhibitors may include small molecule organic compounds, simple or complex sugars, peptides, dominant negative mutants of proteins involved in mucomone binding, signal transduction, and transcription, and other compounds. LPS antagonists can include Lipid A analogs, lipid X analogs and other diglucosamine analogs, and other compound types. Inhibitors of transcription factors include, for example, inhibitors of NF-κB, AP1, AP2, and C/EBP. Signal transduction inhibitors include inhibitors of src, ras, raf1, mek1/2, erk1/2, and rsk. Inhibitors of src that are effective inhibitors of mucomone-induced mucin production include pyrazolopyrimidine (PP1) and a dominant negative mutant of src. Inhibitors of ras that are effective inhibitors of mucomone-induced mucin production include a dominant negative mutant of ras, Ras N17 (Feig et al. (1988) *Mol. Cell. Biol.* 8:2472). Inhibitors of mek1/2 that are effective inhibitors of mucomone-induced mucin production include a PD98059 (Aless et al. (1993) *J. Biol. Chem.* 270:27489) and a dominant negative mutant of mek1/2, HMEK K97R (Minden et al. (1995) *Cell* 81:1147). Inhibitors of erk1/2 that are effective inhibitors of mucomone production include tyrphostin (Novogrodsky et al. *Science* 264:1319) AG126. Inhibitors of rsk that are effective inhibitors of mucomone production include a dominant negative mutant of rsk (Ghoda et al. (1997) *J. Biol. Chem.* 272:21281).

Once it is determined that a compound inhibits mucomone induction of mucin production, useful inhibitors can be selected. Selection criteria are usually based on the extent of modulation produced by the tested compound. Compounds will usually be selected on their ability to inhibit or reduce undesirable mucin production. Such compounds will be useful for the treatment of medical conditions caused by inappropriate mucin production or secretion. Such compounds will also be useful in treating, for example, CF, chronic bronchitis, bronchial pneumonia or bronchial asthma. Typically, compounds that inhibit mucomone-induced mucin production by at least 10%, preferably by at least 30% and more preferably by at least 70% compared to control mucomone-induced mucin production (that is, mucin production in the absence of test compound) will be selected as useful compounds. Such percent inhibition criteria can be applied to other measurements in assays described herein, such as detection of reporter gene activity and RPA assays.

More specific selection criteria can be advantageously used to identify compounds that more specifically modulate a cellular process. It will be recognized that the affinity of the compound being tested for its receptor can often dictate the specificity of the compound, such as a compound with an affinity for a cellular tyrosine kinase, protein kinase A, MAP kinase, LPS, LPS binding protein, or an LPS receptor. Consequently, it is desirable to select compounds that bind to receptors or modulate function with a high apparent or actual affinity. In the case of tyrosine kinase inhibitors, affinities of $10^{-3}$ or less are typical under physiological conditions, $10^{-5}$ or less are preferred, and $10^{-6}$ are more preferred. To achieve such desired results, new compounds or known tyrosine kinase inhibitors or LPS antagonists can be synthesized and screened at predetermined concentrations. Typically, compound concentrations will be 500 micromolar or less, preferably 50 micromolar or less, more preferably 10 micromolar or less, even more preferably 1 micromolar or less and most preferably 0.1 micromolar or less. The percentage inhibition criteria discussed herein can be applied to these concentration selection criteria.

Many different types of tyrosine kinase inhibitors (TKIs) can be tested for inhibitory activity of mucomone-induced mucin production. Such TKIs are described herein and known in the art. Tyrosine kinases are typically classified as either receptor tyrosine kinases or non-receptor tyrosine kinases. Some TKIs inhibit both types of tyrosine kinases and some TKIs, such as, for example, pyrazolopyrimidine (PP1) are specific for non-receptor tyrosine kinases. Often, the TKI will either bind to the ATP or tyrosine site on the tyrosine kinase. Many chemical structures that mimic ATP or tyrosine binding to the tyrosine kinase can be used. For molecules that bind to the ATP site (ATP analogs), it is desirable to test compounds that comprise at least an adenosine base or adenosine base derivative. For molecules that bind to the tyrosine site (tyrosine analog), it is desirable to test compounds that comprise at least a substituted benzene ring, such as (HO)n-benzene-X, where X can be a stable moiety of 1 to 30 atoms, usually comprised of N, S, C, O, or H atoms. TKIs that are identified as inhibitors of mucomone-induced mucin production can be used for the other methods described herein.

Although not necessary for the practice of the present invention, a test compound identified in the reporter gene assay can be assessed for inhibitory activity in vivo assays. In vivo assays and measurements can be used to further select for useful compounds. Alternatively, an in vivo assay can be used to identify compounds alone or prior to an in vitro assay. For example, a test compound can be assayed in vivo by examining its ability to inhibit mucin production in the airway of an animal upon exposure to a mucomone. Alternatively, transgenic animals comprising the mucomone-inducible reporter gene construct can be used in an in vivo assay. Such transgenic animals will be exposed to mucomone in any appropriate fashion in the presence and absence of a test compound and reporter gene activity evaluated by the methods described herein.

The present invention recognizes that mucomones can directly induce mucin production by epithelial cells, such as airway cells. Consequently, the methods of the invention are directed to inhibiting inappropriate mucin production using compounds, such as, for example, small molecule organic compounds, simple or complex sugars, peptides, other inhibitors of signal transduction components, transcription factors, and mucomone binding, and other compounds as described herein and are known in the art that have been identified as inhibitors of mucin production. Such cells include airway secretory cells, reproductive tract epithelial cells, ciliated cells, epithelial cells of the respiratory tract and reproductive tract epithelial cells. Delivery of such inhibitors will depend on the area to be treated. For example, treatment of the respiratory tract can be achieved via aerosol or oral application. Intravenous application is a useful mode of delivery and is sometimes preferred in emergency cases.

The invention includes a method of inhibiting mucin production in an animal, comprising: administering an effective amount of an inhibitor compound to the animal. In a particular embodiment the method is directed to inhibiting mucin overproduction in the airway of an animal by administering an effective amount of an inhibitor compound to target airway cells. An inhibitor compound is identified as described herein. Typically, the inhibitor compound can, at a concentration of 500 $\mu$M or less, inhibit at least 10% of total mucin production from cultured epithelial cells capable of mucomone induced mucin production, preferably HM3 or HCIH292 cells, cultured under conditions conducive to mucin production and in the presence of a mucomone, compared to untreated cells. Preferably, the compound inhibits at least 30% and most preferably at least 70% total mucin production at concentrations of preferably 50 $\mu$M or less, more preferably 10 $\mu$M or less, even more preferably 1 $\mu$M or less, and most preferably 0.1 $\mu$M or less.

Compositions for aerosol and enteral, especially oral, and for parenteral administration are especially preferred. The compositions comprise an inhibitor of mucomone induced mucin production alone or, preferably, together with a pharmaceutically acceptable carrier. The dosage of the inhibitor depends upon the disease to be treated and upon the species, its age, weight and individual condition, and also upon the mode of administration.

Preferred is a pharmaceutical composition suitable for administration to a warm-blooded animal, especially a human, suffering from a medical condition described herein, for example CF, chronic bronchitis, bronchial asthma or bronchial pneumonia, comprising an inhibitor compound described herein, or a salt thereof when salt-forming groups are present, in an amount effective for the inhibition of the mucomone induced mucin production, together with at least one pharmaceutically acceptable carrier.

Preferably, the compounds of the invention are formulated for pulmonary administration. One such method of administration involves the aerosolization of a solution containing, preferably, an aqueous-soluble compound of the invention. Aerosol compositions can alternatively include the active compound packaged in reverse micelles or liposomes. Pharmaceutical compositions suitable for such a method of administration can additionally include aerosol propellants and a surfactant. Examples of small compounds administered by this method can be found in U.S. Pat. Nos. 5,364,615, 5,292,499, and 5,238,683, which are herein incorporated by reference. Both phospholipid and nonconventional liposomes are rapidly becoming accepted as pharmaceutical agents which improve the therapeutic value of a wide variety of compounds (*Cancer Res.* 43:4730 (1983)) and can be applied to tyrosine kinase inhibitors identified by methods of the present invention.

Compounds with poor solubility in aqueous systems require formulation by using solubilizing agents such as ionic surfactants, cholates, polyethylene glycol (PEG), ethanol, or other agents which may have undesirable effects when used for inhalation. In addition, a treatment requiring successful delivery into alveoli of the lower pulmonary region may preclude from the formulation the use of certain irritants such as chlorofluorocarbons and should involve a minimum number of required doses. Alternatively, to avoid such limitations, liposomes or hydrophobic particles can be used. An inhalation formulation providing for a sustained release of such a compound using aerosol droplet particles approximately 1–2.1 $\mu$ in size, preferably less than 1 $\mu$, would satisfy these special needs.

Small particle aerosol liposomes and liposome-drug combinations for medical use have been previously disclosed in EP 87309854.5, which is herein incorporated by reference. Conventional liposomal formulations sometimes have an uncontrollable and fast release rate and frequently have larger particle sizes than are useful for directing a drug to alveoli. However, nonconventional liposomes, which are formed solely by cholesterol and cholesterol derivatives, or alternatively amphipathic lipid components, have been used successfully with controllable sustained release, improved solubility, high encapsulation, absence of need for multiple dosing, and extended stability. Suitable liposomal formulations for sustained release of such compounds include sodium cholesterol sulfate:cholesterol:compound % molar ratios of 55:40:5; 50:40:10; 53:37:9, and most preferably 50:40:10 (U.S. Pat. No. 5,049,389), which is hereby incorporated by reference.

The pharmaceutical compositions comprise from approximately 5% to approximately 95% active ingredient, dosage forms in single dose form preferably comprising from approximately 20% to approximately 90% active ingredient and dosage forms that are not in single dose form preferably comprising from approximately 5% to approximately 20% active ingredient Unit dose forms, such as dragées, tablets or capsules, comprise from approximately 0.05 g to approximately 1.0 g of active ingredient.

The pharmaceutical compositions of this invention are prepared in a manner known per se, for example by means of conventional mixing, granulating, confectioning, dissolving or lyophilizing processes. For example, pharmaceutical compositions for oral use can be obtained by combining the active ingredient with one or more solid carriers, optionally granulating a resulting mixture, and, if desired, processing the mixture or granules, if appropriate with the addition of additional excipients, to form tablets or dragée cores.

Suitable carriers include fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Orally administrable pharmaceutical compositions also include dry-filled capsules consisting of gelatin, and also soft, scaled capsules consisting of gelatin and a plasticizer, such as glycerol or sorbitol. The dry-filled capsules may contain the active ingredient in the form of granules, for example in admixture with fillers, such as corn starch, binders and/or gildants, such as talc or magnesium stearate, and optionally stabilizers. In soft capsules, the active ingredient is preferably dissolved or suspended in suitable liquid excipients, such as fatty oils, paraffin oil, liquid polyethylene glycols or fatty acid esters of ethylene or propylene glycol, to which stabilizers and detergents, for example of the polyoxethylen-sorbitan fatty acid ester type, may also be added.

Other oral dosage forms are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

For parenteral administration compositions include suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

The invention relates also to a method of treating pathological conditions associated with inappropriate mucin production and responsive to the inhibition of mucin production. The compounds of this invention can be administered prophylactically or therapeutically, preferably in an amount effective against the said diseases, to a warm-blooded animal, for example a human, requiring such treatment, the compounds preferably being used in the form of pharmaceutical compositions. In the case of an individual having a body weight of about 70 kg the daily dose administered is from approximately 1 mg to approximately 5000 mg, preferably from approximately 20 mg to approximately 500 mg, of a compound of this invention.

The following examples are offered by way of illustration and not by way of limitation. Variation and alternate embodiments will be apparent to those of skill in the art.

EXAMPLES

Identification of the 5' MUC-5AC regulatory region

Cell Culture—The human lung epithelial carcinoma cell line NCIH292 was grown in RPMI 1640 medium supplemented with 10% heat-inactivated fetal calf serum (Gibco). In some experiments, cells were exposed for 6 h to $P.$ aeruginosa to increase their content of MUC 5AC mRNA.

cDNA Synthesis and 5' RACE—PCR—Two sources were used to prepare RNA for cDNA synthesis, $P.$ aeruginosa-exposed NCIH292 cells and human stomach tissue. The sequences of the primers used for PCR are shown in Table 1. The RNA was prepared by the method of Chomczynski and Sachi ((1987) Anal. Biochem. 162:156–159). Total RNA (3 $\mu$g) was used to generate double-stranded (ds) cDNA using the Marathon cDNA Amplification kit (Clontech). The ds cDNA was ligated with the Marathon cDNA adaptor and purified on a chromaspin +TE-1000 column (Clontech) in a total volume of 100 $\mu$l. 5' RACE (Rapid Amplification of cDNA Ends, Frohman, (1991) Meth. Enzymol. 218:340–362) was performed using the ds cDNA as template with one HGM-1 gene-specific primer (GM1) and the adaptor primer AP1 or AP2. Additional gene-specific primers (GM5, GM9, GM9G, and GM9H) were generated based on the sequences of progressively amplified 5' RACE products.

translation start site. Following this is a secretory protein signal sequence. The entire ORF encodes 1100 amino acids. The nucleotide sequence is approximately 65% similar to the MUC 2 amino terminal sequence. No tandem repeat

TABLE 1

| Name | Sequence | Location |
| --- | --- | --- |
| 5' RACE PCR | | |
| GM1 | GGCCGTGGAGGATGCTGCACTGCTTCT (SEQ ID No. 3) | 3348/3322 |
| GM5(a) | GATGAAGCCAACACTGCAGGTGATGTCCC (SEQ ID No. 4) | 2255/2227 |
| GM9 | AGAAGTGGGCACCTCCAAAGCACAGAGC (SEQ ID No. 5) | 1374/1348 |
| GM9G | AAGTCCCCACAGAGCCCACAGGTCTTG (SEQ ID No. 6) | 688/662 |
| GM9H(b) | TGTGTGCCGGGTGCAGGCCAGAGCGAGAG (SEQ ID No. 7) | 119/90 |
| AP1 | CCATCCTAATACGACTCACTATAGGGC (SEQ ID No. 8) | Adapter |
| AP2 | ACTCACTATAGGGCTCGAGCGGC (SEQ ID No. 9) | Adapter |
| Probes for Northerns and genomic library screening | | |
| NP3a 5' | TGCTATTATGCCCTGTGTAGCCAGGACTGCC (SEQ ID No. 10) | 580/610(c) |
| NP3a 3' | TCACAGCCGGGTACGCGTTGGCACAAGTGGG (SEQ ID No. 11) | 871/841(c) |
| TER | GGACAGGGCACTCTTCCCCGCCGTCCAC (SEQ ID No. 12) | 17/44 |
| GM5 | GATGAAGCCAACACTGCAGGTGATGTCCC (SEQ ID No. 13) | 2255/2227 |
| GM9 | AGAAGTGGGCACCTCCAAAGCACAGAGC (SEQ ID No. 14) | 1374/1348 |
| GM2.6 | GGCACGCGTGACACCAAATACGCCAACAAGACCTGTCCC (SEQ ID No. 15) | 639/674 |
| RNase protection and primer extension | | |
| RPA-T7 | GGATCCTAATACGACTCACTATAGGGAGGTATGCCGGGTGCAG GCCA (SEQ ID No. 16) | 113/100 |
| RPA-5' | GTGAGCACCCACTGTTTACTTGG (SEQ ID No. 17) | -123/-101 |
| GM9H | TGTGTGCCGGGTGCAGGCCAGAGCGAGAG (SEQ ID No. 18) | 119/90 |
| Genomic walking | | |
| GM9H5 | CTTCCTCCGGCCAACACTCATTGTGTGGAC (SEQ ID No. 19) | 68/39 |
| AP1 | GTAATACGACTCACTATAGGGC (SEQ ID No. 20) | Adapter |
| AP2 | ACTATAGGGCACGCGCTGGT (SEQ ID No. 21) | Adapter |

(a) Also used for northern
(b) Also used for primer extension
(c) Numbered according to Klomp, et al. (1995)

In the first round of 5' RACE-PCR, an HGM-1-specific primer (GM1) and an adaptor primer (AP1) were used. This amplification yielded a 900 bp PCR fragment. Sequence data showed that this fragment was the 5' extension of human gastric mucin (HGM) (Klomp, et al. (1995), *Biochem. J.* 308:831–8 and was >65% similar to the MUC 2 D-domain 3 just 5' to the central repeat region. Primer GM5 was designed based on the 5' end of this fragment and was used in a second round of 5' RACE-PCR. This generated an 1100 bp PCR fragment whose 5' end was used to design primer GM9. When used in a third round of 5' RACE-PCR, GM9 generated a 700 bp fragment. Primer GM9G was designed based on the 5' end of this fragment and was used in a fourth round of RACE-PCR to generate a 600 bp fragment. Primer GM9H, 103 bp downstream of the 5' end of the fourth round RACE-PCR product, was used in a fifth round of RACE PCR and generated a 110 bp product. Repeated efforts to generate larger products with primer GM9H from both gastric tissue and NCIH292 (airway) cell cDNA yielded PCR products with identical sequence that were ~100 bp in length. This suggested that GM9H was approximately 100 bp from the 5' end of the mRNA as processed in both gastric tissue and NCIH292 cells.

The overall cDNA sequence obtained by 5' RACE is shown in FIGS. 5 and is about 3.3 KB (SEQ ID No. 2). There is an open reading frame (ORF) of 3300 nucleotides, 290 of which directly overlap and are in frame with those encoding human gastric mucin. At +48 is an ATG codon embedded in a Kozak consensus sequence. This is a putative sequence is present, but there are three cysteine-rich domains (D1–D3) in which the cysteine positions correspond almost exactly to those in the amino terminal of human MUC 2.

Northern blot analysis of tissue distribution of RACE—PCR product cognate RNA—Total RNA was extracted from human tissues and cultured cells according to previously described methods (Chomczynski and Sachi (1987) *Anal. Biochem.* 162:156–159. RNA samples (20 µg) were separated on 1.0% agarose gels containing 2.2 M formaldehyde and then transferred to a positively charged nylon membrane (Gene Screen, NEN, Dupont). cDNA probes were labeled with $\alpha$-$^{32}$P dCTP using a BRL random primer labeling kit. For the MUC 5AC 3' end, probes were amplified using primers NP3a 5' and NP3a 5'; for the new sequence MUC 5AC-5'RP, probes were amplified using primers TER and GM9. Labeled probe was added to 10 ml of hybridization buffer containing 50% formamide, 10% dextran sulfate, 0.2% Denhardt's, 50 mM TRIS-HCI, pH 7.5, 1 M NaCl and 0.1% sodium pyrophosphate to give a concentration of 2–5×10$^6$ cpm/ml. Membrane hybridization and washing were performed using conditions described previously (Ohmori, et al. (1994) *J. Biol. Chem.* 269:17833–40).

Identical hybridization patterns were obtained when blots were probed with a probe from the C-terminal cDNA, NP3a, (Meerzaman, et al. (1994), *J. Biol. Chem.* 269:12932–12939) or with a probe from the newly cloned N-terminal sequence.

DNA Sequencing—Fragments amplified by RACE-PCR were purified by low-melting point agarose gel electrophoresis, cut with appropriate restriction enzymes and cloned into pBluescript II SK⁻ (Stratagene) or sequenced directly. E. coli (SURE strain, Stratagene) were transformed with plasmids containing these fragments. Transformants were grown at 37° C. or 30° C. Both sense and anti-sense strands were sequenced. Sequencing reactions were carried out using SequiTherm Long-Read Cycle Sequencing kits (Epicentre Technologies) and Thermo Sequenase Fluorescent Labeled Primer Cycle Sequencing kits (Amersham Life Science) with the IRD41 (Li-cor) labeled primers. Sequence data were assembled by Lasergene software (DNAstar). Homology and transcription factor binding site searches were performed using MatInspector release 2.1 and Transcription Element Search Software (TESS, University of Pennsylvania) and MacVector software (IBI).

Chromosome localization of PCR-amplified DNA fragments—Two mouse/human hybrid cell line DNA panels were purchased from Bios. Cell line 1049 contained human chromosomes 5 and 11. Cell line 1079 contained human chromosomes 2 and 5. DNA from each cell line was used as a PCR template with RACE product primers to determine the chromosomal location of RACE products. MUC 5AC-5' primers amplified a product from mouse-human hybrid cell line 1049, but not from cell line 1079. As both cell lines contained DNA from chromosome 5 but only 1049 contained DNA from chromosome 11, the results clearly show that the RACE product MUC 5AC-5'RP maps to chromosome 11.

Primer extension analysis of transcription start site—When progressive 5' RACE reactions could no longer amplify additional sequence from either the stomach tissue or airway cell (NCIH292) cDNA templates, primer extension using primer GM9H (approximately 100 bp from the putative 5' end of the mRNA) was carried out to confirm that the transcription start site had been reached. Primer extension was done using the Promega AMV reverse transcriptase (AMVRT) primer extension system. Briefly, 0.1 pmole of $^{32}$P end labeled primer GM9H was incubated with 5 µl (40–50 µg) total RNA from tissue or cells and 5 µl of 2×PE buffer at 58° C. for 20 min. After cooling to room temperature, 9 µl of a master mix containing 2×PE buffer, 6.25 mM sodium pyrophosphate and 1 µl AMV RT was added to each sample. After a 30 min. incubation at 42° C., the samples were diluted with 20 µl loading dye, denatured by heating for 10 min at 90° C. and run on a 6% acrylamide, 7M urea, TBE gel, along with sequencing ladder and size markers.

The primer extension reaction yielded a product of 114 bp when RNA from stomach tissue or airway cells was used as a template supporting the view suggested by RACE-PCR that the transcription start site was approximately 100 bp upstream of primer GM9H.

RNase protection analysis of transcription start site—To confirm transcription start site location as determined by RACE-PCR and primer extension assays, RNase protection assays were performed. The labeled RNA probe required for this assay was generated from a PCR product designed to incorporate the T7 promoter. This PCR fragment was amplified from a 12 kb genomic clone (7"A) derived from screening a human genomic library in the Lambda FIX II vector (Stratagene) and was known from sequencing data to contain the putative exon I of MUC 5AC. The library was screened with a probe generated from PCR of a 5' RACE product with primers GM9 and GM2.6 using methods described in Ohmori, et al., (1994). The primers used to generate the RNA probe template from the genomic clone were RPA-T7 containing sequence from exon I and the T7 promoter and primer RPA-5' containing upstream genomic sequence (see Table 1). This enabled the generation of a high specific activity $^{32}$P-UTP labeled RNA probe using T7 RNA polymerase. For the assay, 50 µg of total RNA was hybridized with 5×10⁵ cpm of probe overnight at 42° C. The RNA:RNA template was digested for 15 min. at room temperature with 0.5 units of RNase A and 20 units of RNase T1, precipitated and run on a 6% polyacrylamide/urea sequencing gel with a sequencing ladder for size determination.

A total of three RNA samples were examined. These samples were taken from gastric tissue, colon carcinoma cells (HM3) and lung carcinoma cells (NCIH292). RNA from each sample protected the same three probe fragments, indicating putative start sites at one, six and eight bp upstream of the start site predicted by primer extension. The start site predicted by computer program NNPP (promoter prediction by neural network, Lawrence Berkeley National Laboratory, Human Genome Center) was at 4 bp upstream of the site indicated by primer extension. As it fell approximately in the middle of the range of possible start sites, the computer-predicted start site was designated as +1.

5' genomic DNA walking—Genomic DNA was amplified from DNA provided in the Human PromoterFinder™ DNA Walking kit (Clontech) according to instructions provided by the manufacturer. Long sequence amplifications were carried out with the LA PCR kit (TaKaRa) and High Fidelity Expand PCR kit (Boehringer Mannheim) using primers GM9H5' and adaptor primers AP1 and AP2.

These amplifications yielded an approximately 4 KB genomic DNA fragment containing 3753 nucleotides 5' to the MUC 5AC transcription start site identified above. The sequence is shown in FIG. 1A and B (SEQ ID No. 1). The sequence from −300 to +1 as well as downstream sequence through exon 1 (+1 to +120) has been confirmed by sequencing a subclone of genomic clone 7"A. The upstream sequence contains a TATA box at −28/−31, further supporting the view that the RACE-PCR product MUC 5AC-5'RP is at the 5' end of the mRNA and that the designated transcription start site, +1 is accurate. Present in the putative promoter region are NF kappa B sites (at −216 through −228 and −950 through −959), Sp-1 sites (at −149 through −154 and −76 through −84), GRE site (at −311 through −316 and −1253 through −1258), AP-2 sites (at −458 through −463 and −1098 through −1103), PEA site (at −930 through −935) and CACCC box (at −65 through −70) sites.

Example 2

Construction of Reporter Gene Construct

A DNA fragment extending from −3752bp to +68 bp was cloned into the MluI/SmaI site of the pGL3 vector (Promega). pGL3 contains a luciferase gene downstream from the SmaI site. This construct, referred to as M4-2, was deposited with the American Type Culture Collection as ATCC designation 98701. M4-2 was co-transfected with pcDNA3, containing the neomycin resistance gene, into the epithelial cell line HM3. G418-selected colonies were pooled, expanded, and used in luciferase assays.

A DNA fragment, synthesized by PCR, extending from −614 bp to +68 bp was cloned into pGL3 in a similar fashion. This construct is referred to as −614 construct.

Example 3

Activation of Reporter Gene Construct by Environmental Tobacco Smoke

HM3 colon carcinoma cells (Kuan, et al. (1987) Cancer Res. 47:5715–5724) or NCIH292 lung carcinoma cells (Levine, et al. (1995) Am. J. Respir. Disease 12:196–204) were transfected with the 4.0 Kb MUC 5AC reporter gene construct, M4-2, or the −614 construct from Example 2. Transfection was carried out essentially as described in Felgner et al. (1987), supra. In brief, 2 μl lipofectamine and 1 μg DNA were added to approximately 5×10⁶ cells in 100 μl of Optimen (Gibco) and incubated at room temperature for about 30 minutes. The mixture was then diluted to 1 ml and added to one culture well of a 6 well plate. G418-selected colonies were pooled, expanded and used in luciferase assays.

Environmental tobacco smoke was used as a mucomone. Culture medium DME-F12 (Dulbecco's Modified Eagle's:Ham's F12 at 1:1) was exposed to tobacco smoke at various concentrations, for 6 hours. Exposure of the medium was carried out in open culture dishes in an enclosed container into which tobacco smoke produced by burning cigarettes was introduced in a controlled manner. Smoke concentration was measured in units of total suspended particles/ml (TSP/ml). Transfected cells were transferred into the smoke-exposed medium (in 6-well plates, 5×10⁵ cells per well) and incubated for various times. The cells were then harvested, lysed and the luciferase activity determined as described in Li et al. (1997).

FIG. 2 shows the results of an experiment using HM3 cells transfected with the 4.0 Kb MUC 5AC construct, M4-2, and incubated in smoke-exposed medium for 6 hr., 14 hr. or 21 hr. The medium was exposed to three concentrations of smoke: 8.5 TSP/ml, 17 TSP/ml and 34 TSP/ml. The control cells were treated in an identical manner but were not exposed to smoke medium. The relative luciferase activity (RLA) was measured in light units.

Relative luciferase activity increased with both time of exposure of the cells to smoke medium and concentration of smoke used to prepare the smoke medium. At the highest level of smoke concentration tested (34 TSP/ml) at 21 hr, the RLA was 8–9 fold higher than the control level.

FIG. 3 shows the results of an experiment using NCIH292 cells transfected with the M4-2 construct and incubated in smoke-exposed medium for 6 hr and 14 hr with the same three smoke concentrations as for the HM3 cells above.

NCIH292 cells transfected with the −614 construct also showed increased luciferase activity after culture in smoke-exposed medium although the magnitude of the increase was not as large as that of the M4-2 transfected cells.

Example 4

Inhibition of Mucomone-induced Reporter Gene Activation

Several possible inhibitors of mucomone-induced mucin production were tested for their effect on the smoke induced luciferase activity described in Example 3. Inhibitors tested included the inhibitors Genistein (Calbiochem), anti-MEK (PD98059; Alessi et al. 1995), PKC-I (Bisindolymaleimide) and PKA-I (KT 5720, Calbiochem). HM3 cells transfected with the 4.0 KB MUC 5AC construct, M4-2, were incubated in smoke-exposed medium as described in Example 3. The inhibitors were added to the cells at the concentrations indicated in Table 2 for various times before the cells were transferred to the smoke medium. Additional inhibitor was added to the smoke medium after the cells were transferred. The results are shown in FIG. 4. For each inhibitor tested, the RLA was lower in cells exposed to inhibitor than in cells not exposed to inhibitor, indicating that the smoke-induced luciferase activity was inhibited.

TABLE 2

| Inhibitor | Concentration | Times Before Addition of Smoke-Medium |
|---|---|---|
| Bisindolymaleimide | 2.5 nM to 10 nM | 1 hr |
| KT 5720 | 0.1 to 0.5 μM | 15 min - 1 hr |
| Genistein | 30 μM | 30 min - 2 hr |
| PD98059 | 50–100 μM | 1 hr |

Example 5

Activation of Reporter Gene Constructs containing a heterologous promoter.

Additional reporter gene constructs were made containing the MUC 5AC 5' regulatory region from −3752 bp to −143 bp ("long") or from −3752 bp to −3535 bp ("short") joined upstream of a minimal thymidine kinase (tk) promoter which was operably joined to a luciferase reporter gene (coding sequence). The tk promoter-luciferase construct was described in Li et al., Proc. Natl Acad. Sci USA, 95:5718 (1998). Exposure of the constructs to environmental tobacco smoke was carried out as described in Example 3. Both the long and the short MUC 5AC fragments conferred comparable smoke inducibility on the tk promoter of approximately 15-fold over control. Control constructs without the MUC 5AC fragments did not show inducibility upon exposure to smoke. These results suggest that one or more smoke response elements are present in the MUC 5AC 5' regulatory region between −3752 bp and −3535 bp (SEQ ID No. 1 from nucleotide 1 to 218).

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated polynucleotide molecule comprising at least 20 consecutive nucleotides of the MUC 5AC mucin gene 5' regulatory region (SEQ ID NO:1), or a complement thereof.

2. The polynucleotide molecule of claim 1 comprising at least 50 consecutive nucleotides of the MUC 5AC mucin gene 5' regulatory region (SEQ ID NO:1), or a complement thereof.

3. The polynucleotide molecule of claim 1 comprising at least 100 consecutive nucleotides of the MUC 5AC mucin gene 5' regulatory region (SEQ ID NO:1), or a complement thereof.

4. The isolated polynucleotide molecule of claim 1, having the sequence of SEQ ID NO: 1, or the complement thereof.

5. The isolated polynucleotide molecule of claim 1, selected from the group consisting of a polynucleotide molecule having the sequence of SEQ ID NO.: 1 from nucleotide 1 to nucleotide 218, a polynucleotide molecule having the sequence of SEQ ID NO.: 1 from nucleotide 2392 to nucleotide 3752, and a polynucleotide molecule having the sequence of SEQ ID NO.: 1 from nucleotide 3139 to nucleotide 3752, and complements thereof.

6. An isolated polynucleotide molecule comprising a mucomone response element of the MUC 5AC mucin gene 5' regulatory region.

7. The polynucleotide molecule of claim 6, wherein said mucomone response element comprises at least 20 consecutive nucleotides from SEQ ID NO:1.

8. The polynucleotide molecule of claim 7, wherein said mucomone response element comprises a polynucleotide molecule selected from the group consisting of a polynucleotide molecule having the sequence of SEQ ID NO.: 1 from nucleotide 1 to nucleotide 218, a polynucleotide molecule having the sequence of SEQ ID NO.: 1 from nucleotide 2392 to nucleotide 3752, and a polynucleotide molecule having the sequence of SEQ ID NO.: 1 from nucleotide 3139 to nucleotide 3752, and complements thereof.

9. A mucomone-inducible reporter gene construct comprising:

a mucomone response element from the 4 KB MUC 5AC mucin gene 5' regulatory region and a responsive promoter, operably linked to a reporter gene.

10. The reporter gene construct of claim 9, wherein said responsive promoter is a mucin promoter.

11. The reporter gene construct of claim 10, wherein said mucin promoter is a MUC 5AC promoter.

12. The reporter gene construct of claim 9, wherein said reporter gene is selected from the group consisting of chloramphenicol acetyl transferase, beta-galactosidase, β-glucoronidase, firefly luciferase, bacterial luciferase, alkaline phosphatase and green fluorescent protein.

13. The reporter gene construct of claim 9, wherein said mucomone response element comprises at least 50 consecutive nucleotides of the MUC 5AC mucin gene 5' regulatory region (SEQ ID NO:1).

14. The reporter gene construct of claim 9, wherein said mucomone response element comprises at least 100 consecutive nucleotides of the MUC 5AC mucin gene 5' regulatory region (SEQ ID NO:1).

15. The reporter gene construct of claim 9, wherein said construct is M4-2.

16. The reporter gene construct of claim 9, wherein said mucomone response element comprises a polynucleotide molecule selected from the group consisting of a polynucleotide molecule having the sequence of SEQ ID NO: 1 from nucleotide 1 to nucleotide 218, a polynucleotide molecule having the sequence of SEQ ID NO.: 1 from nucleotide 2392 to nucleotide 3752, and a polynucleotide molecule having the sequence of SEQ ID NO.: 1 from nucleotide 3139 to nucleotide 3752, and complements thereof.

17. The reporter gene construct of claim 9, wherein said responsive promoter is a thymidine kinase promoter.

18. An epithelial cell comprising the reporter gene construct of claim 9.

19. The cell of claim 18, wherein said reporter gene construct is stably transfected into the chromosome of said cell.

* * * * *

SEQUENCE LISTING

```
<160> NUMBER OF SEQ ID NOS: 22

<210> SEQ ID NO 1
<211> LENGTH: 3835
<212> TYPE: DNA
<213> ORGANISM: Homo sapiens

<400> SEQUENCE: 1
```

-continued

```
ggtcgacggc ccgggctggt ctggacccca gcagcggccc tgggtgacgt ctggctgagg      60
gaggagaaag ctgtggctgg ggcggcaagg cctgggtggc cagttggcca ggtgccccgg     120
ggcttggccc agcctcagac acgcaggggg cactcccctc tgagggccac gctggtgact     180
cagactgttc agaggtcacg gtatggactg ggccagtgac tcaggcctgt cctctgttgg     240
gggctggaca ctgactcacc cactgcctcc tgtctatctg agggcgtaag gagggcaggc     300
cttcaggcac tcacatgcgg ccctggccag ggtcccggtc acacctgcag accctcaagc     360
ccttccctat gccccactga cataaccacc tggccctggg atctggtccc accgcggggc     420
ccattgtcca ctaccaggac cctcctctgc cttcatcagc accaggcgac ctggtgtcca     480
ctcctgggcc agggcagggg aaccctggct cacctggtc gagtcagacc tcccgaagca      540
ccagtggctg gggtggtcca ccctaaccct gtcagccgct cagccttaaa tgtgatcact     600
cgctcagtca gtcgccaccc actcactcac tcacccactc acttattcac tcactcaccc     660
actcacttat tcacccattc actcattcac tcacccattc actcactcac ttattcactc     720
actctctcac tcattcatta attcgcccat tcactcacac tttcactcac tcacttattc     780
actcatacac tcattcactt atttactcac tcattcactc actcattaat tcacccattc     840
actcactcac ttattcactc atagactcat acactcactc attcactcac gcatccactc     900
attcactcac tcatttaccc actcattcac tcattcactc actcactcat ttattcaccc     960
attcactcat tcattcactc actcactgac tcattgactc attccctcac tcattcaccc    1020
attcacttac tcattcactc acccatttat tcactcactc actcatttac tcattcattc    1080
acccattcac tcactcactg actcattgac tcattcactc attcacccat tcacttactc    1140
actcactcat ttactcactc attcattcat tgactcatta actcattccc tctctcattc    1200
actcactcac tgactcatta actcattcac tctctcatgc atccactcat tcactcactc    1260
actgactcac tcattcactc actcattgac tcactcattt ggttattcac tcattcactc    1320
actcactgac tcattcactc actcattcac tgctcactta ttcactcttt cactatctct    1380
ttcattcaca ttcattcatt aactcagtca ctcactcatt cactctcact cattcactta    1440
ctcatttact cattcactca tctattcatt cactcattca ctcactcatt cattcaccca    1500
ttcactcatt cattcaccca ttcactcact cacttattca ctcatagact catacactca    1560
ctcactcatt gactcactca ctcattcact catgcatcca ctcattcact cactcattta    1620
ctcactcact cactcatcca ctcactcact cattcattca cccattcact caatcattca    1680
ttcactcact cactgactca ttgactcatt ccctcactca ttcacccatt cacttattca    1740
ttcactcacc catttattca ctcactcact catttactca ctcactcact catttactca    1800
ttccattcac ccattcactc actcattcac tcactcacta actcattgac tcattcactc    1860
actcattccc ccttcactta ctcactaact tatttactca ctcattcact cactcattca    1920
ttgactcatt aactcattca ctctttcact cactcactga ctcattcact cattcactca    1980
ctcattcact cactcaccca ctcattgact cactcattca cttattcact cattcactca    2040
ctcactgact cattcactca ttcactgctt gcttattcac tctttcacta tctctctcat    2100
tcacatttat tcattaactc agtcactcac tcattcactc tctcattcac ttactcattt    2160
actcactcat ttactcattc actctctcat tcacttactc atttactcac tcatttactc    2220
actcactcac ctgttcactc actcgctcac tcattcacat tcattttaac tcactcattt    2280
actcatagac tcactcattt atccactcac ttattcatta cctcattcat tcactcactc    2340
aatcattttc cctttcccca cactcctgcc acatgtgaag tgctctttct ctaggcacct    2400
```

-continued

```
gggctaagac aggacatggg gagggaaagg cacagaaatg gagaagtagg caatcataaa    2460
gagcttggga cgggtcccta gagagctgga agcaagtgct cagaacagcc ttgaggcacc    2520
tcttcgaccc taacccctct gcagcaggac aaagggccca gcccagcctc tcccttcct     2580 gccattcctc ccatgggaga ccttctggtt ggacgctcca catgggcagt ggagcagccg    2640
accttggctg gggagtgtgt ggctgcctgg gagggagagt ctagccacag tgtccagcca    2700
cacacctgtg gtctgggcaa gtgttcatca cacaacagca ccttctcagc cagagccctt    2760
caggccaaag actcactggg acctttctgt gctgggactg ctcggaccag tcaacagctt    2820
cctgtccaga gggtactgag catttctgga tcttggtggc cagagaccat caagtgactt    2880
gaactggccc tgcccgcctg gggtcaggag acagaagcac aggtggactc ctgggcaatg    2940
ctgggagggg gctgcatggt gagggagggg ttctatcatt tgcctggagg ctgctgccag    3000
gagcccctct ccagggaggg tgaggctggc tggcgctact tcagtggcag catgtggctg    3060
gcctgaggga cgccttggct cactcactcc tcaatcactc atttactcat tcattcactc    3120
actcaatcat ttttccttc gccacactcc tgccgcatgt gctctctctc taggcatccg     3180
ggtaagacaa gacatgggga gtaaaaggca cagaaatgga gaaataggtg accataagga    3240
gctttggatg gggctgggc tggcctctcc ctcccaggca gccacacatt ccccagccaa     3300
ggtcggcagc tccactgccc atgtggaggg tccaaccagg aggtcggcca tgggaggaat    3360
ggcaggaaag ggaaaggctg ggctgggccc cctgtcctgc tgcagaggga ttagtgtcaa    3420
agaggtgcct taaggctgtt ctgagcactc acttctgggc accaggaact cacaggctgc    3480
tgggcatggc acggtgccca gggagagtct agggtgggt atgtggggag accccctgca    3540
ggccagggct tgggggggcc ctcggaaact gggctctacc cggcagacac acccatctcc    3600
gcctgccacc ggccgctggc cagcccgcag tgagcaccca ctgtttactt gggtgagggg    3660
gaaccacagg ccccgccctg cccacccacg tgaagcacgg ggctggagcc agctctgggg    3720
ctacaaaaag ctcctgccac cttgggtccc tcctcagagg ctgctgaggg acagggcact    3780
cttccccgcc gtccacacaa tgagtgttgg ccggaggaag ctggccctgc tctgg         3835
```

<210> SEQ ID NO 2
<211> LENGTH: 3358
<212> TYPE: DNA
<213> ORGANISM: Homo sapiens

<400> SEQUENCE: 2

```
ctcagaggct gctgagggac agggcactct tccccgccgt ccacacaatg agtgttggcc      60
ggaggaagct ggccctgctc tgggccctgg ctctcgctct ggcctgcacc cggcatacag     120
ccatgcccag gatggctcct ccgaatccag ctacaagcac caccctgccc tctctgccta    180
tcgcccgggg gcccagcggg gtcccgctcc gtggggcgac tgtcttccca tctctgagga    240
ccatccctgt ggtacgagcc tccaacccgg cgcacaacgg gcgggtgtgc agcacctggg    300
gcagcttcca ctacaagacc ttcgacggcg acgtcttccg cttccccggc ctctgcaact    360
acgtgttctc cgagcactgc ggtgccgcct acgaggattt taacatccag ctacgccgca    420
gccaggagtc agcggccccc acgctgagca gggtcctcat gaaggtggat ggcgtggtca    480
tccagctgac caagggctcc gtcctggtca acggccaccc ggtcctgctg cccttcagcc    540
agtctggggt cctcattcag cagagcagca gctacaccaa ggtggaggcc aggctgggcc    600
ttgtcctcat gtggaaccac gatgacagcc tgctgctgga gctggacacc aaatacgcca    660
```

```
acaagacctg tgggctctgt ggggacttca acgggatgcc cgtggtcagg gagctcctct    720
cccacaacac caagctgaca cccatggaat tcgggaacct gcagaagatg gacgacccca    780
cggagcagtg tcaggaccct gtccctgaac ccccgaggaa ctgctccact ggctttggca    840
tctgtgagga gctcctgcac ggccagctgt tctctggctg cgtggccctg gtggacgtcg    900
gcagctacct ggaggcttgc aggcaagacc tctgcttctg tgaagacacc gacctgctca    960
gctgcgtctg ccacacccttg ccgagtact cccggcagtg cacccatgca gggggttgc   1020 cccaggactg gcggggccct gacttctgcc ccagaagtg ccccaacaac atgcagtacc   1080
acgagtgccg ctcccctgt gcagacacct gctccaacca ggagcactcc cgggcctgtg   1140
aggaccactg tgtggccggc tgcttctgcc ctgaggggac ggtgcttgac gacatcggcc   1200
agaccggctg tgtccctgtg tcaaagtgtg cctgcgtcta caacggggct gcctatgccc   1260 cagggggccac ctactccaca gactgcacca actgcacctg ctccggaggc cggtggagct   1320
gccaggaggt tccatgcccg ggtacctgct ctgtgcttgg aggtgcccac ttctcaacgt   1380
ttgacgggaa gcaatacacg gtgcacggcg actgcagcta tgtgctgacc aagccctgtg   1440
acagcagtgc cttcactgta ctggctgagc tgcgcaggtg cgggctgacg gacagcgaga   1500
cctgcctgaa gagcgtgaca ctgagcctgg atggggcgca gacggtggtg gtgatcaagg   1560
ccagtgggga agtgttcctg aaccagatct acacccagct gcccatctct gcagccaacg   1620
tcaccatctt cagaccctca accttcttca tcatcgccca gaccagcctg ggcctgcagc   1680
tgaacctgca gctggtgccc accatgcagc tgttcatgca gctggcgccc aagctccgtg   1740
ggcagacctg cggtctctgt gggaacttca acagcatcca ggccgatgac ttccggaccc   1800
tcagtggggt ggtggaggcc accgctgcgg ccttcttcaa caccttcaag acccaggccg   1860
cctgccccaa catcaggaac agcttcgagg acccctgctc tctgagcgtg gagaatgaga   1920
agtatgctca gcactggtgc tcgcagctga ccgatgccga cggcccttc ggccggtgcc   1980 atgctgccgt gaagccgggc acctactact cgaactgcat gtttgacacc tgcaactgtg   2040
agcggagcga ggactgcctt gtgcgccgcg ctgtcctcct acgtgcacgc ctgtgcgcca   2100
agggcgtgca gctcggcggc tggagggacg gcgtctgcac gaagcctatg atcacttgcc   2160
ccaagtcaat gacgtaccac taccatgtca gcgcctgcca gcccacctgc cgctccctga   2220
gcgaggggga catcacctgc agtgttggct tcatccccgt ggatggctgc atctgtccca   2280 agggcaccttt cctggacgac acgggcaagt gtgtgcaggc cagcaactgt ccctgctacc   2340
acagaggctc catgatcccc aatggggagt cggtgcacga cagcgggct atctgcacct   2400 gcacacatgg gaagctgagc tgcatcggag gccaagcccc cgccccagtg tgtgctgcgc   2460
ccatggtgtt ctttgactgc cgaaatgcca cgcccagggg cacagggct ggctgtcaga   2520 agagctgcca cacactggac atgacctgtt acagccccca gtgtgtgcct ggctgcgtgt   2580
gccccgacgg gctggtggcg gacggcgagg gcggctgcat cactgcggag gactgcccct   2640
gcgtgcacaa taaggccagc taccgggccg gccagaccat ccgggtgggc tgcaacacct   2700
gcacctgtga cagcaggatg tggcggtgca gatgaccc ctgcctggcc acctgcgccg   2760
tgtacgggga cggccactac ctcaccttcg acggacagag ctacagcttc aacggagact   2820
gcgagtacac gctggtgcag aaccactgtg gcgggaaaga cagcacccag gactcctttc   2880
gtgttgtcac cgagaacgtc ccctgcggca ccacaggac cacctgctcc aaggccatca   2940 agatttttcct ggggggcttc gagctgaagc taagccatag gaaggtggag gtgatcggga   3000
```

```
cggacgagag ccaggaggtg ccatacacca tccggcagat gggcatctac ctggtggtgg   3060
acaccgacat tggcctggtg ctgctgtggg acaagaagac cagcatcttc atcaacctca   3120
gccccgagtt caagggcagg gtctgcggcc tgtgtgggaa cttcgacgac atcgccgtta   3180
atgactttgc cacgcggagc cggtctgtgg tggggacgt gctggagttt gggaacagct    3240
ggaagctctc ccctcctgc ccagatgccc tggcgcccaa ggaccctgc acggccaacc     3300 ccttccgcaa gtcctgggcc cagaagcagt gcagcatcct ccacggcccc accttcgc    3358
```

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:SYNTHETIC

<400> SEQUENCE: 3
ggccgtggag gatgctgcac tgcttct                                        27

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:SYNTHETIC

<400> SEQUENCE: 4
gatgaagcca acactgcagg tgatgtccc                                      29

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:SYNTHETIC

<400> SEQUENCE: 5
agaagtgggc acctccaaag cacagagc                                       28

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:SYNTHETIC

<400> SEQUENCE: 6
aagtccccac agagcccaca ggtcttg                                        27

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:SYNTHETIC

<400> SEQUENCE: 7
tgtgtgccgg gtgcaggcca gagcgagag                                      29

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:SYNTHETIC

```
<400> SEQUENCE: 8
ccatcctaat acgactcact atagggc                                            27

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:SYNTHETIC

<400> SEQUENCE: 9
actcactata gggctcgagc ggc                                                23

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:SYNTHETIC

<400> SEQUENCE: 10
tgctattatg ccctgtgtag ccaggactgc c                                       31

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:SYNTHETIC

<400> SEQUENCE: 11
tcacagccgg gtacgcgttg gcacaagtgg g                                       31

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:SYNTHETIC

<400> SEQUENCE: 12
ggacagggca ctcttccccg ccgtccac                                           28

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:SYNTHETIC

<400> SEQUENCE: 13
gatgaagcca acactgcagg tgatgtccc                                          29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:SYNTHETIC

<400> SEQUENCE: 14
agaagtgggc acctccaaag cacagagc                                           28

<210> SEQ ID NO 15
```

<211> LENGTH: 39
<212> TYPE: DNA
<213> ORGANISM: Artificial Sequence
<220> FEATURE:
<223> OTHER INFORMATION: Description of Artificial Sequence:SYNTHETIC

<400> SEQUENCE: 15
ggcacgcgtg acaccaaata cgccaacaag acctgtccc                    39

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence:SYNTHETIC

<400> SEQUENCE: 16
ggatcctaat acgactcact atagggaggt atgccgggtg caggcca           47

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:SYNTHETIC

<400> SEQUENCE: 17
gtgagcaccc actgtttact tgg                                     23

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:SYNTHETIC

<400> SEQUENCE: 18
tgtgtgccgg gtgcaggcca gagcgagag                               29

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:SYNTHETIC

<400> SEQUENCE: 19
cttcctccgg ccaacactca ttgtgtggac                              30

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:SYNTHETIC

<400> SEQUENCE: 20
gtaatacgac tcactatagg gc                                      22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:SYNTHETIC

<400> SEQUENCE: 21

-continued

```
actatagggc acgcgctggt                                            20

<210> SEQ ID NO 22
<211> LENGTH: 428
<212> TYPE: DNA
<213> ORGANISM: Homo sapiens

<400> SEQUENCE: 22
ccaccttggg tccctcctca gaggctgctg agggacaggg cactcttccc cgccgtccac    60
acaatgagtg ttggccggag gaagctggcc ctgctctggg ccctggctct cgctctggcc   120 tgcaccggc atacaggtac ggcttggccc tgggccctct actggtcctg ggtggtgcgg    180
tactgagtgg gcctcagcag ctcagtcttt gccctgggca ggctgcattg tgccatgaac   240
ggctcccagc agcatagccc ctgactgtgg cctggcagaa cgagcagttt cccttgtggt   300
tgggaaggga tctctgggct tcgcgacctc tgagctggca ttcctgagca ggaagtagag   360
ctcagatctc ggctttcctc tgccgatcct gcactgtccc agaagcgaag actgccacag   420
tatctcag                                                           428
```